US009685744B2

(12) United States Patent
Little et al.

(10) Patent No.: US 9,685,744 B2
(45) Date of Patent: Jun. 20, 2017

(54) MACHINE CASE WITH IMPROVED ELECTRICAL CONNECTOR

(71) Applicant: FOXCONN INTERCONNECT TECHNOLOGY LIMITED, Grand Cayman (KY)

(72) Inventors: Terrance F. Little, Fullerton, CA (US); Chun-Yi Chang, New Taipei (TW); Stephen Sedio, Valley Center, CA (US)

(73) Assignee: FOXCONN INTERCONNECT TECHNOLOGY LIMITED, Grand Cayman (KY)

( * ) Notice: Subject to any disclaimer, the term of this patent is extended or adjusted under 35 U.S.C. 154(b) by 0 days.

(21) Appl. No.: 14/942,975

(22) Filed: Nov. 16, 2015

(65) Prior Publication Data

US 2016/0141814 A1    May 19, 2016

Related U.S. Application Data

(60) Provisional application No. 62/083,159, filed on Nov. 21, 2014, provisional application No. 62/085,478, filed on Nov. 28, 2014, provisional application No. 62/203,865, filed on Aug. 11, 2015, provisional application No. 62/080,250, filed on Nov. 14, 2014.

(51) Int. Cl.
| | |
|---|---|
| *H01R 13/60* | (2006.01) |
| *H01R 13/66* | (2006.01) |
| *H01R 13/73* | (2006.01) |
| *H01R 13/405* | (2006.01) |
| *G06F 1/16* | (2006.01) |

(52) U.S. Cl.
CPC ........... *H01R 13/73* (2013.01); *G06F 1/1632* (2013.01); *H01R 13/405* (2013.01); *A61B 2562/225* (2013.01); *H01R 2201/12* (2013.01)

(58) Field of Classification Search
CPC ........ H01R 13/73; H01R 27/02; H01R 13/60; H01R 4/70
USPC ............... 439/529, 91, 591, 733.1, 638, 885
See application file for complete search history.

(56) References Cited

U.S. PATENT DOCUMENTS 5,479,320 A * 12/1995 Estes ...................... H01R 12/52
361/744
6,077,089 A *  6/2000 Bishop ................. H01R 12/714
439/296

(Continued)

*Primary Examiner* — Hae Moon Hyeon
(74) *Attorney, Agent, or Firm* — Wei Te Chung; Ming Chieh Chang

(57) ABSTRACT

An electrical connector for use within a machine case includes an insulator and a plurality of contacts. The insulator defines opposite top and bottom surfaces thereon in a vertical direction. The contacts are retained to the insulator via an insert molding process. Each of said contacts is stamped and bent from sheet metal and unitarily formed with an upper contacting section exposed upon the top surface, and a lower contacting sections exposed upon the bottom surface. Each of said upper contacting section and said lower contacting section extends along a longitudinal direction perpendicular to both said vertical direction and said transverse direction. Each of the upper contacting section and the lower contacting section is planar and stationary. One of said upper contacting section and said lower contacting section has an outer end exposed to an exterior for originally linking to a contact carrier.

19 Claims, 36 Drawing Sheets

(56) References Cited

U.S. PATENT DOCUMENTS

| | | | |
|---|---|---|---|
| 6,579,104 B1* | 6/2003 | Bishop | H01R 12/714 |
| | | | 439/596 |
| 7,578,700 B2* | 8/2009 | Xiong | H01R 13/65802 |
| | | | 439/606 |
| 9,439,574 B2* | 9/2016 | McCombie | A61B 5/02427 |
| 2009/0023338 A1* | 1/2009 | He | H01R 43/24 |
| | | | 439/607.01 |
| 2012/0296174 A1* | 11/2012 | McCombie | A61B 5/02427 |
| | | | 600/301 |
| 2016/0141771 A1* | 5/2016 | Little | H01R 13/405 |
| | | | 439/577 |
| 2016/0141819 A1* | 5/2016 | Chang | H01R 31/005 |
| | | | 439/529 |

* cited by examiner

US 9,685,744 B2

MACHINE CASE WITH IMPROVED ELECTRICAL CONNECTOR

This application claims the benefit of, and priorities to U.S. Provisional Patent Applications No. 62/080,250, filed Nov. 14, 2014; No. 62/083,159, filed Nov. 21, 2014; No. 62/085,478, filed Nov. 28, 2014; and No. 62/203,865, filed Aug. 11, 2015. The instant application relates to the copending applications titled "ELECTRICAL CONNECTOR FOR USE WITH CRADLE" and "MACHINE CASE WITH IMPROVED TERMINAL MODULE", both having the same applicant and some common inventors with the instant application.

BACKGROUND OF THE INVENTION

1. Field of the Invention

The invention relates to the connector for use within a machine case which connects a plurality of cables via a cradle having the LGA contact connector thereon.

2. Description of Related Art

Wearable medical technology is becoming a hot commodity, as these devices come to market; they have the potential to help both patients and clinicians monitor vital signs and symptoms. The wearable medical device usually comprises a cradle, a machine case attached to the cradle for housing processing module such as processor and associated electronics, and cables with plugs inserted into the cradle. During use, the machine case reversibly snaps into the cradle, upon mating of the cradle and the machine case, interface cavities are formed on the cradle for receiving the plugs of the cables leading to one or more peripheral devices such as sensors which collect data related to the physiological properties of interest, such as heart rate, temperature, SpO2, blood pressure, etc., therefore, the data related to the physiological properties could be presented on the machine case for patients or clinicians monitoring. Thereby, the machine case must mate with the cradle stably so as to electrically connect with the cables reliably.

An machine case with improved electrical connector is designed to solve the aforementioned proposal.

SUMMARY OF THE INVENTION

According to one aspect of the present invention, an electrical connector for use within a machine case includes an insulator and a plurality of contacts. The insulator defines opposite top and bottom surfaces thereon in a vertical direction. The contacts are retained to the insulator via an insert molding process and arranged along a transverse direction perpendicular to said vertical direction. Each of said contacts is stamped and bent from sheet metal and unitarily formed with an upper contacting section exposed upon the top surface, and a lower contacting sections exposed upon the bottom surface. Each of said upper contacting section and said lower contacting section extends along a longitudinal direction perpendicular to both said vertical direction and said transverse direction. Each of the upper contacting section and the lower contacting section is planar and stationary. One of said upper contacting section and said lower contacting section defines an outer end exposed to an exterior for originally linking to a contact carrier.

According to another aspect of the present invention, a machine case comprises a base, a first contact module, and a second contact module. The base has a first deck station and a second deck station respectively located at two opposite ends of the base in a longitudinal direction. The first contact module is seated upon the first deck station and comprises a first insulator defining opposite first top and bottom surfaces thereon in a vertical direction, and a plurality of first contacts retained to the first insulator via a first insert molding process and arranged along a transverse direction perpendicular to said vertical direction and longitudinal direction. Each of said first contacts defines a first upper contacting section exposed upon the first top surface, and a first lower contacting section exposed upon the first bottom surface. Each of said first upper contacting sections extends in a length along the longitudinal direction shorter than that of said lower contacting sections. The second contact module is seated upon the second deck station and comprises a second insulator defining opposite second top and bottom surfaces thereon in said vertical direction, and a plurality of second contacts retained to the second insulator via the first insert molding process and arranged along the transverse direction perpendicular. Each of said second contacts defines a second upper contacting section exposed upon the second top surface, and a second lower contacting section exposed upon the second bottom surface. Each of said second upper contacting sections extends in a length along the longitudinal direction shorter than that of said second lower contacting sections.

Other objects, advantages and novel features of the invention will become more apparent from the following detailed description when taken in conjunction with the accompanying drawings.

DETAILED DESCRIPTION OF THE PREFERRED EMBODIMENT

Figure 1A:
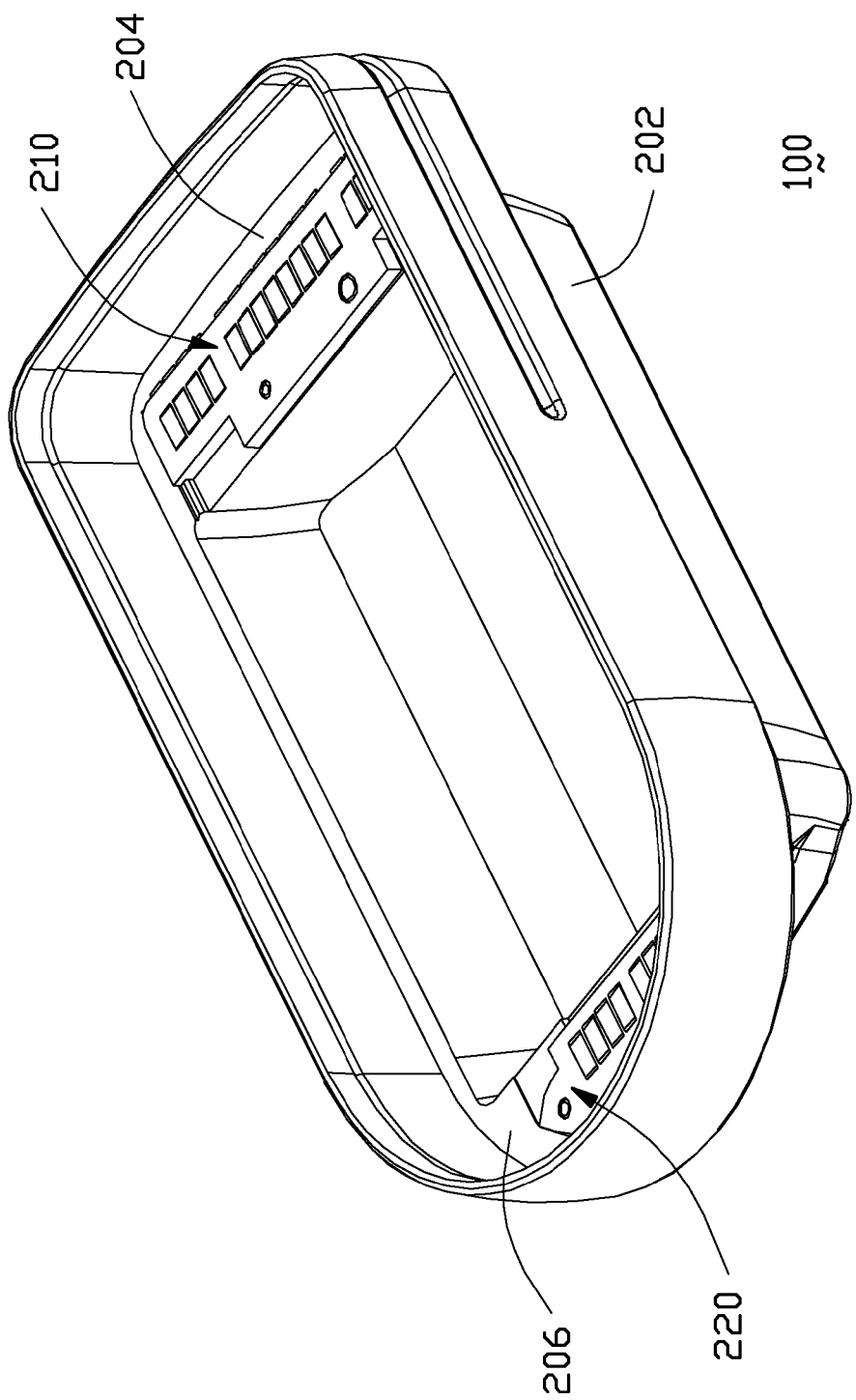
FIG. 1(A) is a downward assembled perspective view of the machine case according to one embodiment of the invention.
Figure 1B:
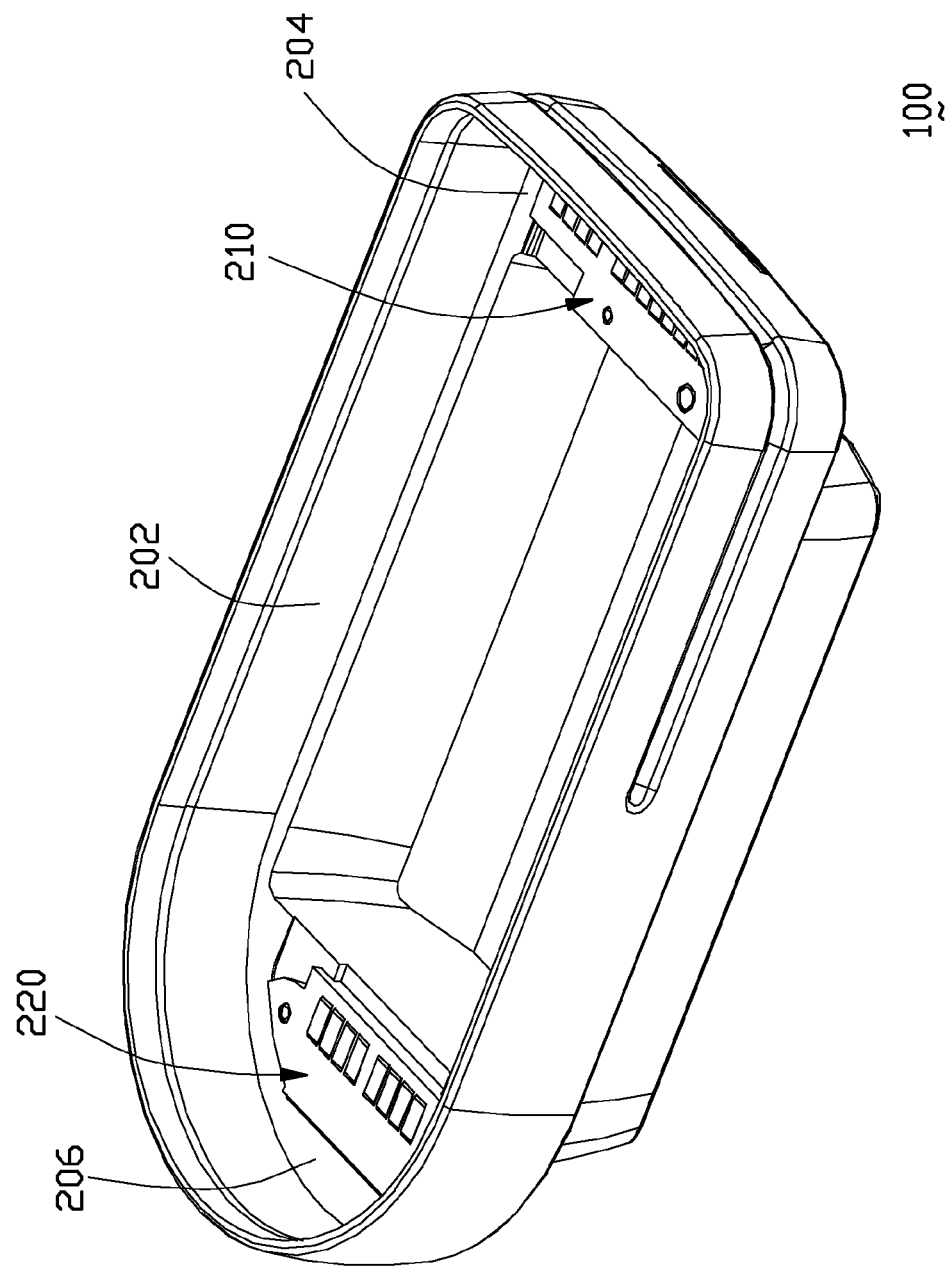
FIG. 1(B) is another downward assembled perspective view of the machine case of FIG. 1(A).
Figure 1C:
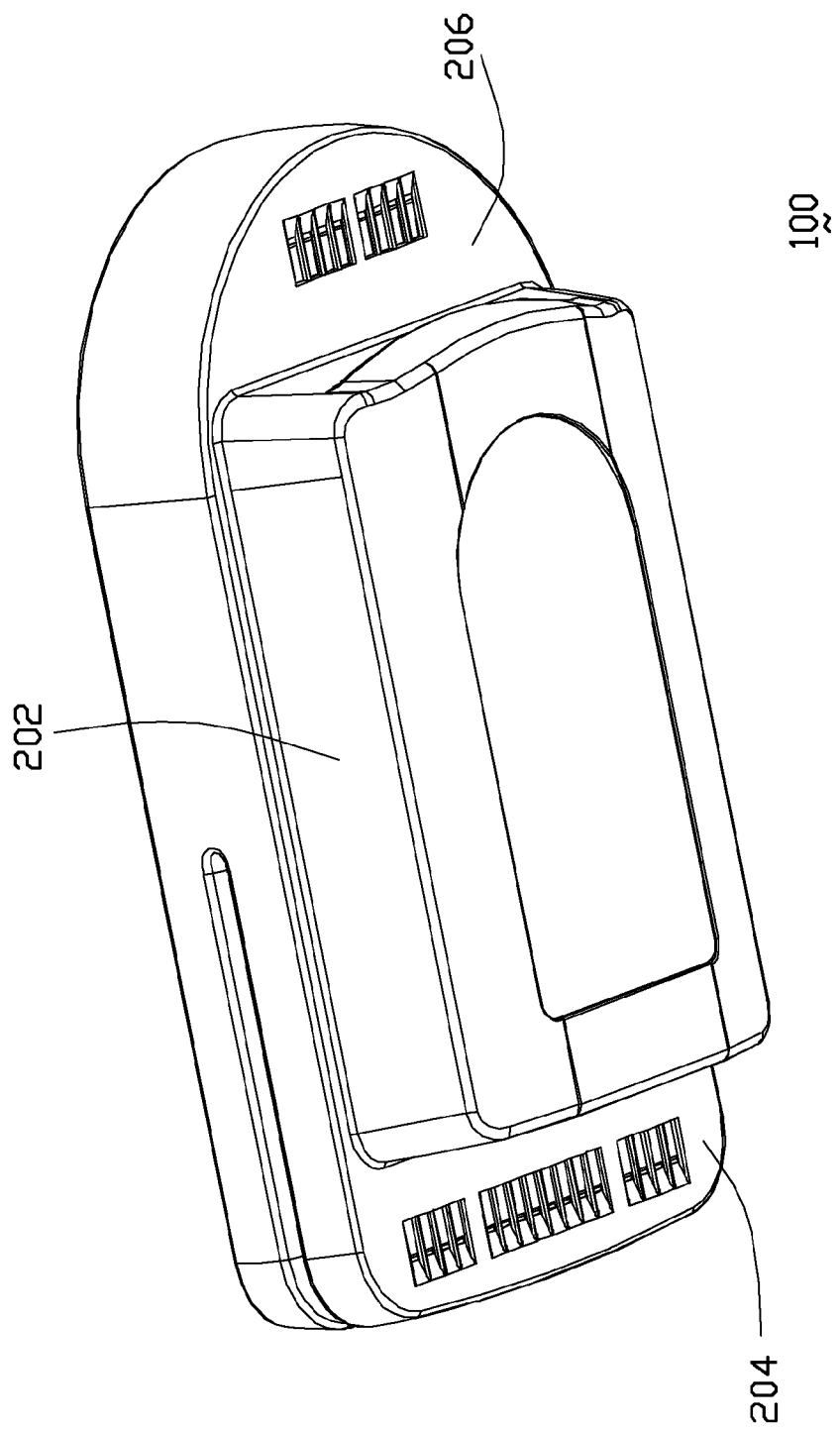
FIG. 1 (C) is an upward assembled perspective view of the machine case of FIG. 1(A).
Figure 2A:
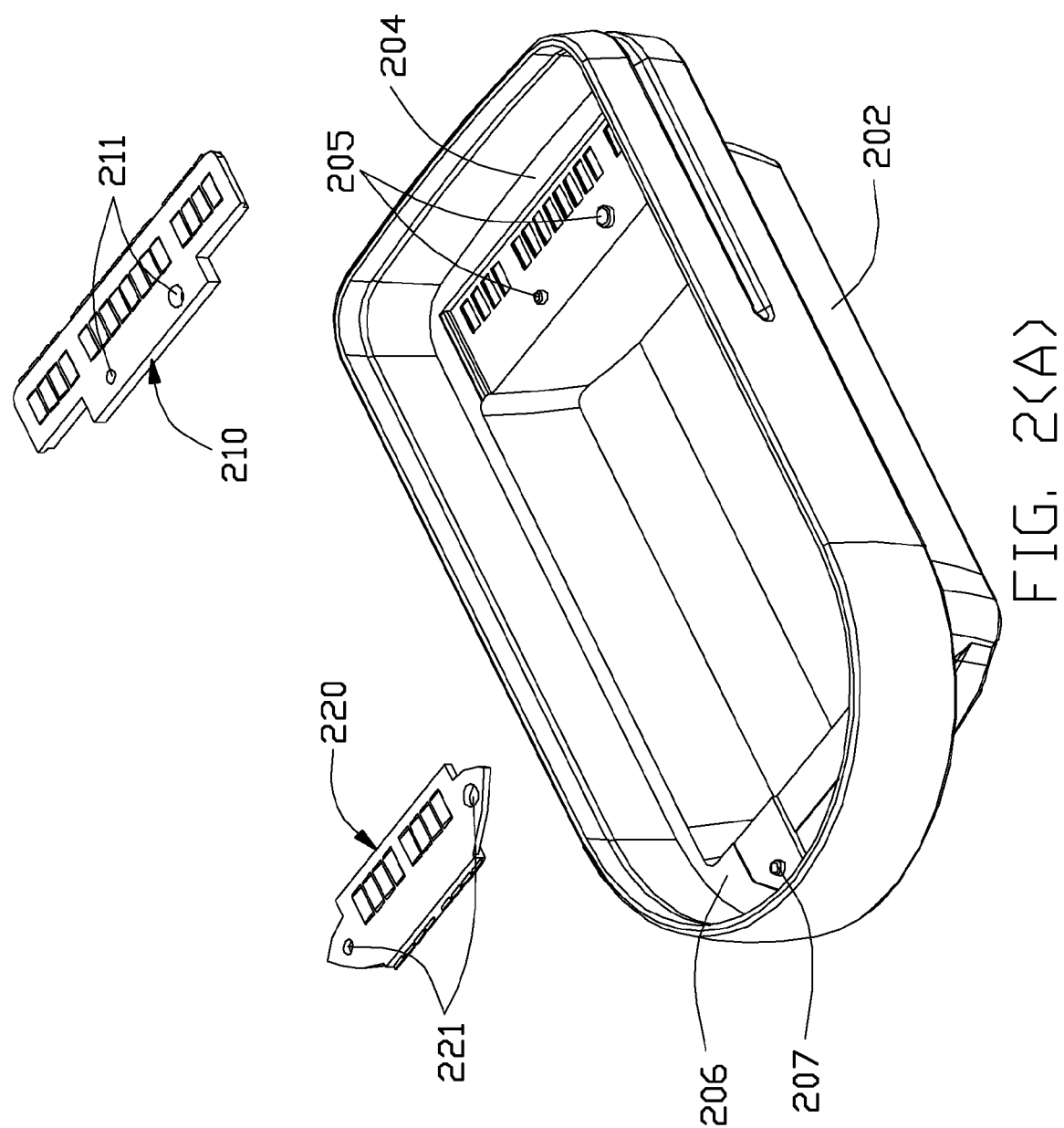
FIG. 2(A) is a downward exploded perspective view of the machine case of FIG. 1(A).
Figure 2B:
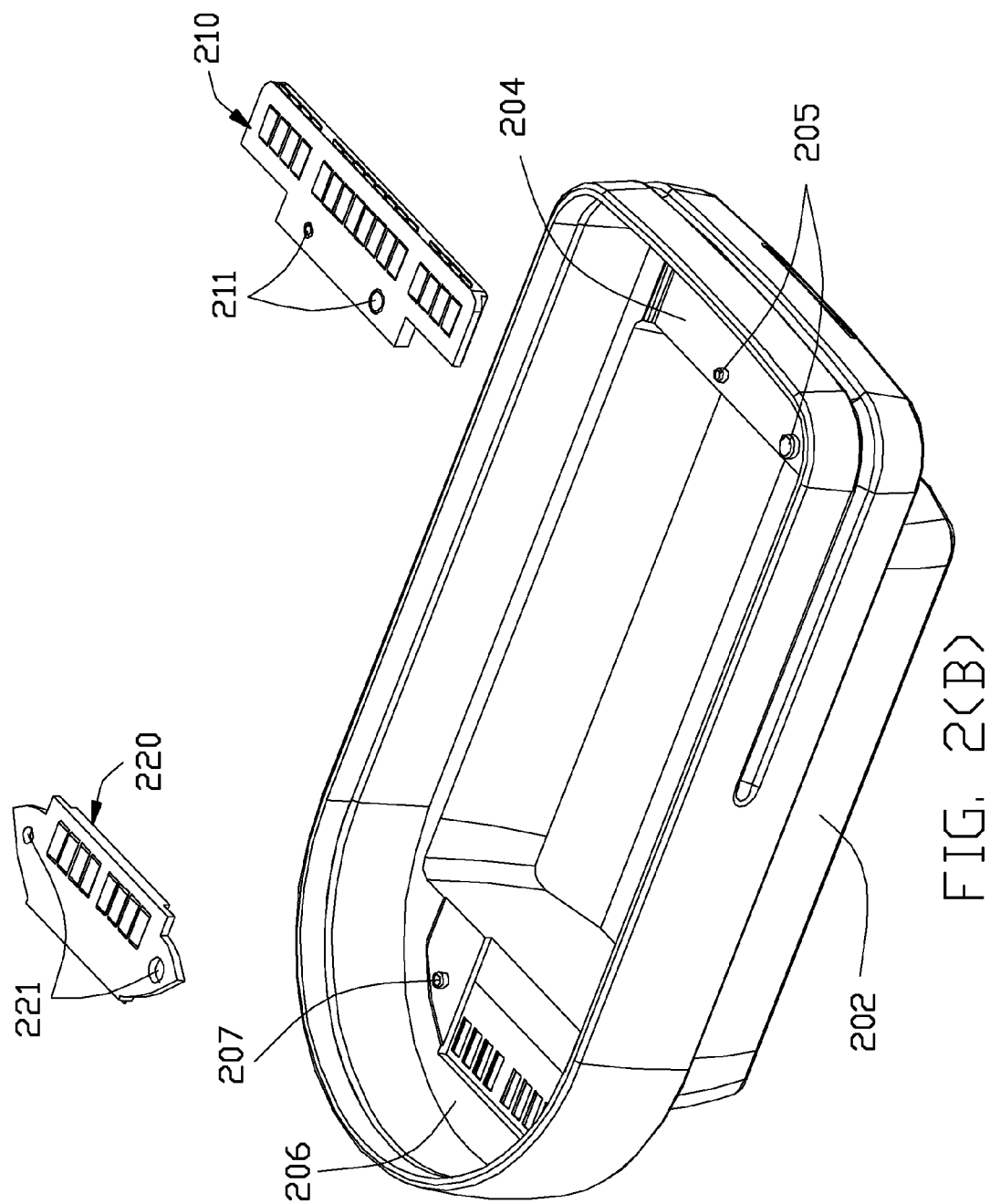
FIG. 2(B) is another downward perspective view of the machine case of FIG. 2(A).
Figure 2C:
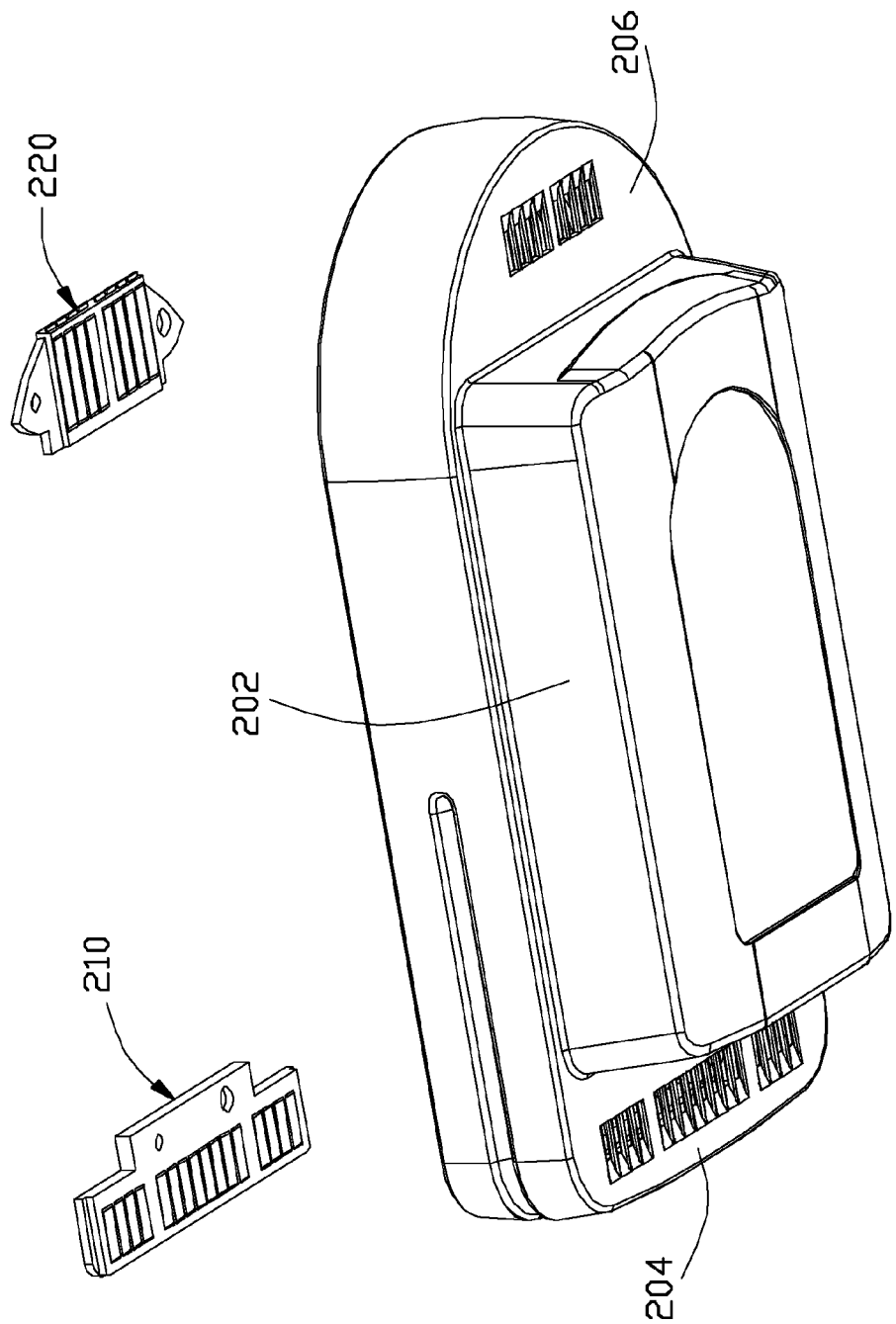
FIG. 2(C) is an upward exploded perspective view of the machine case of FIG. 2(A).
Figure 3A:
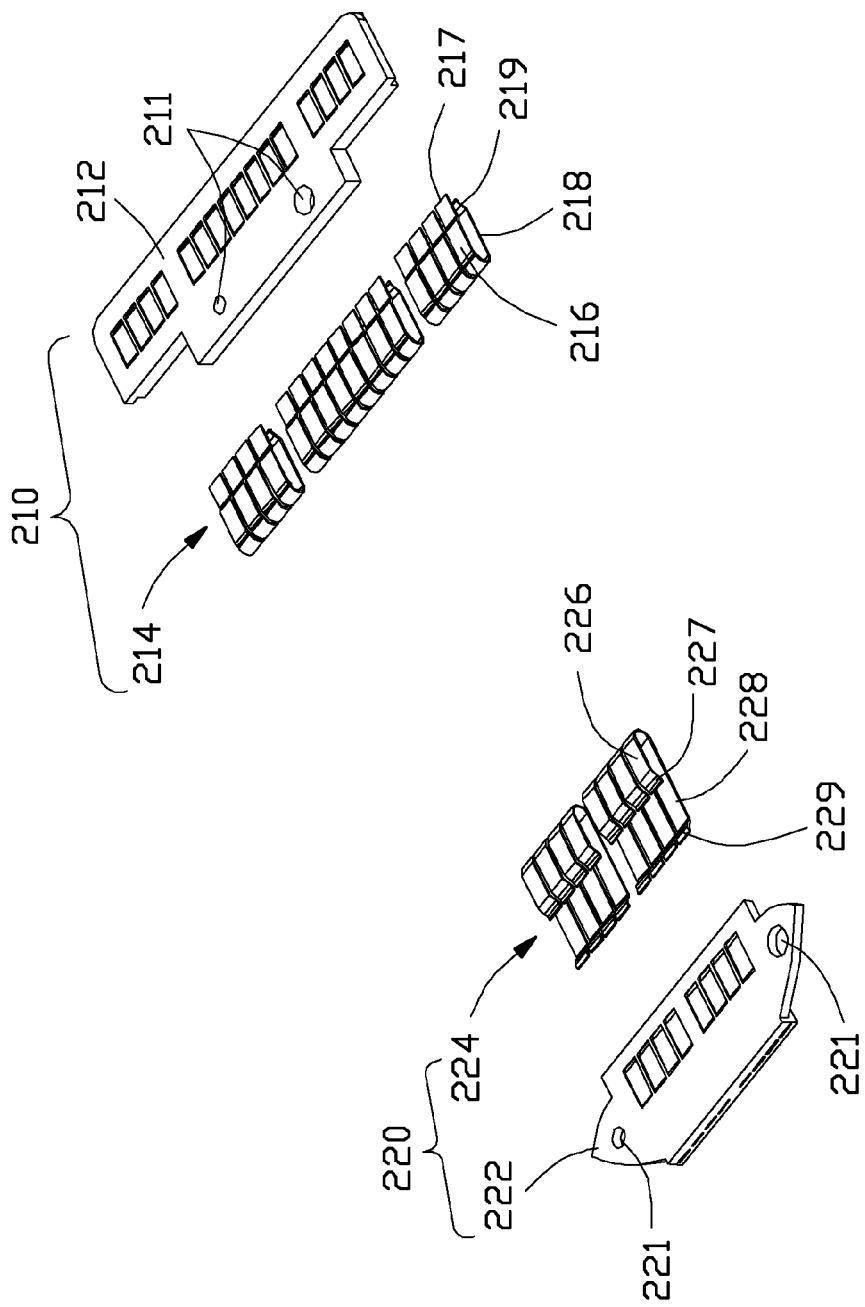
FIG. 3(A) is a downward exploded perspective view of the contact module of the machine case of FIG. 2(A).
Figure 3B:
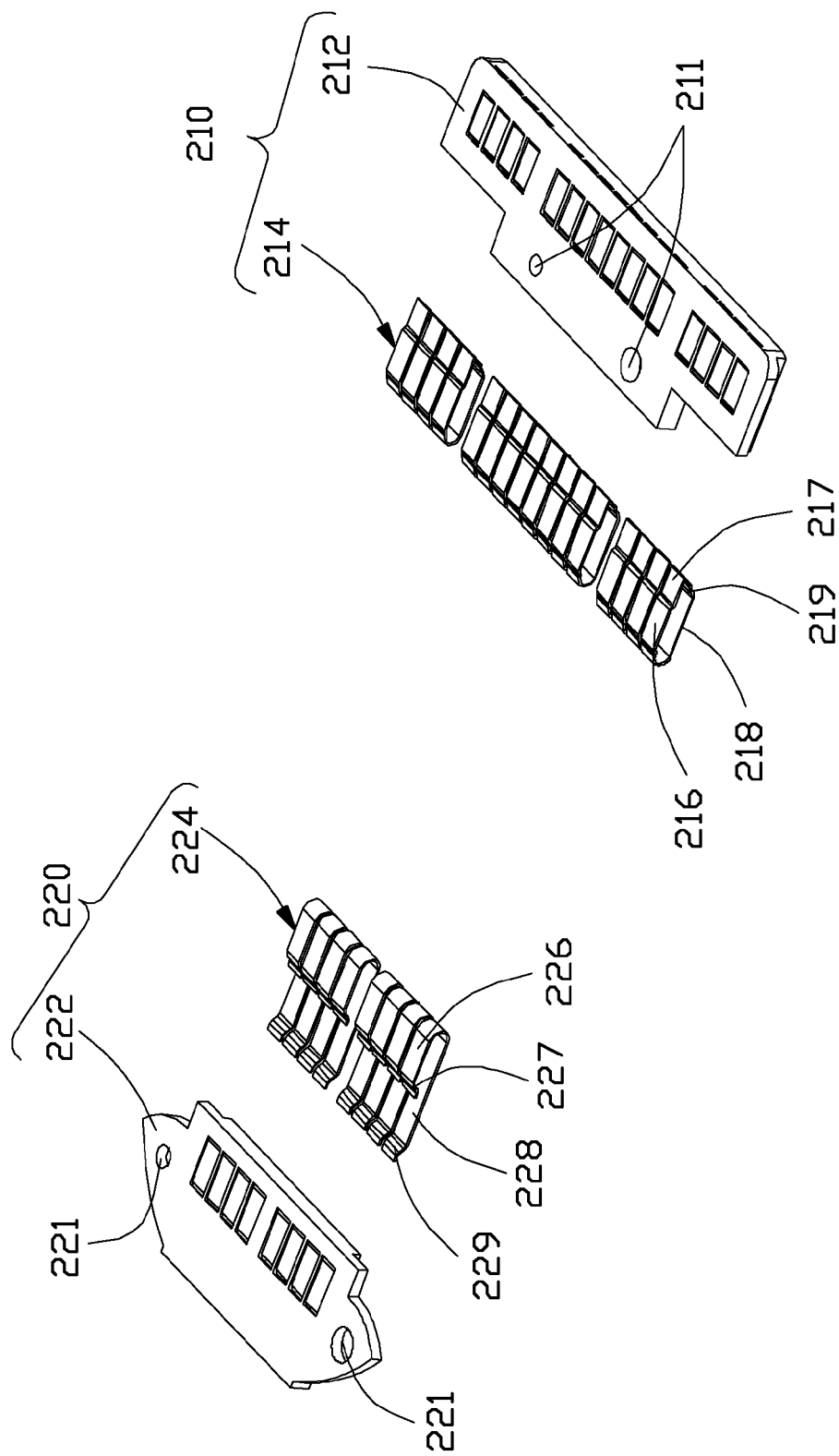
FIG. 3(B) is another downward exploded perspective view of the contact module of FIG. 3(A).
Figure 3C:
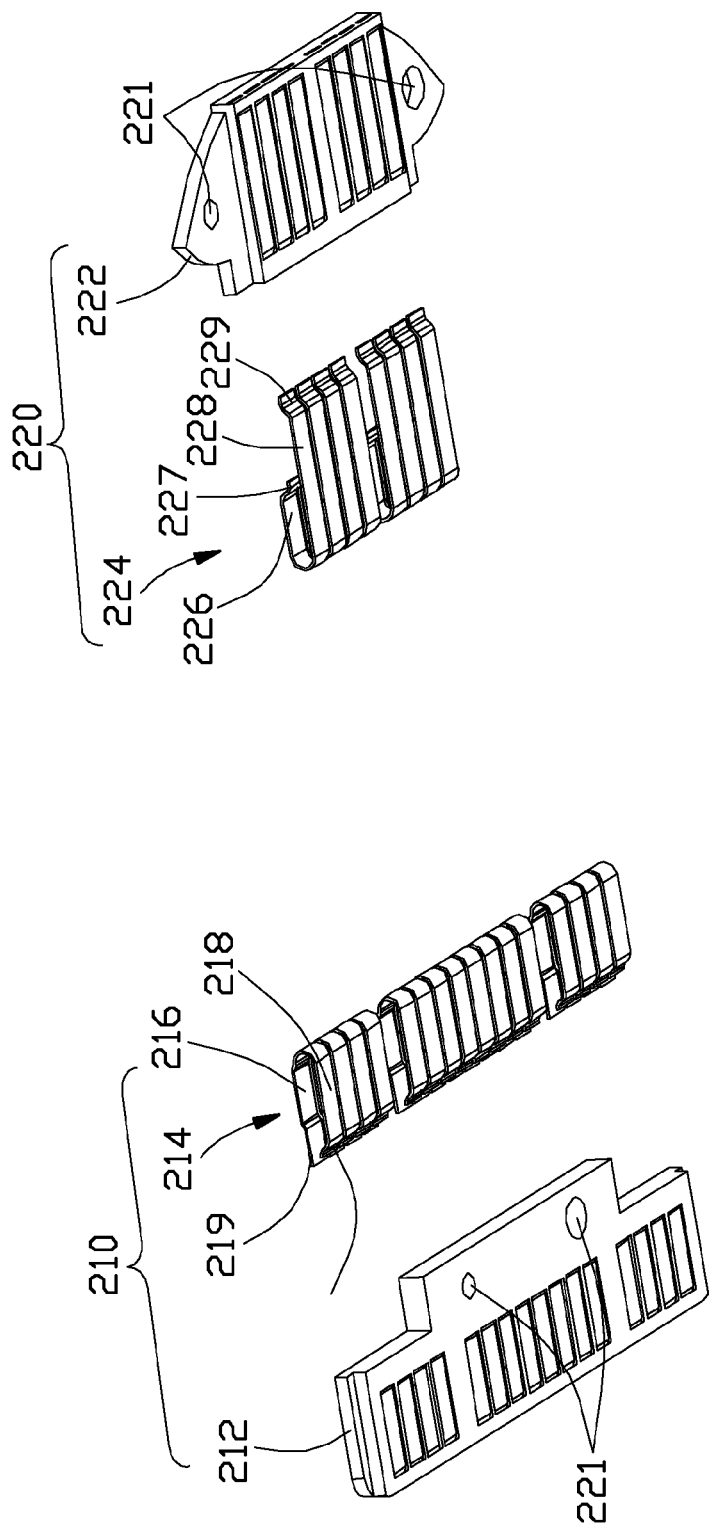
FIG. 3(C) is an upward exploded perspective view of the contact module of FIG. 3(A).
Figure 3D:
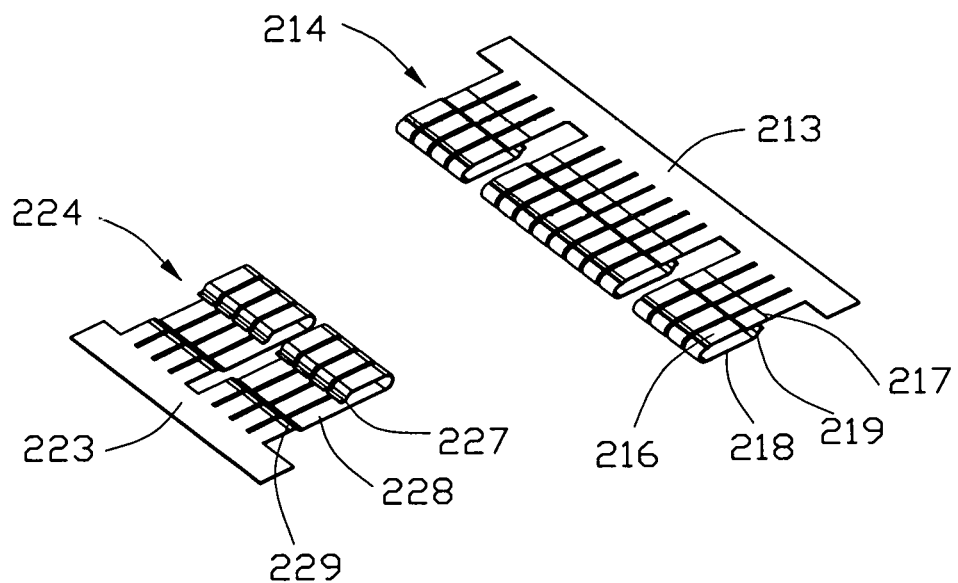
FIG. 3(D) is schematic perspective view showing first and second contacts connected to contact carriers respectively before breaking therefrom during the insert molding process.
Figure 4A:
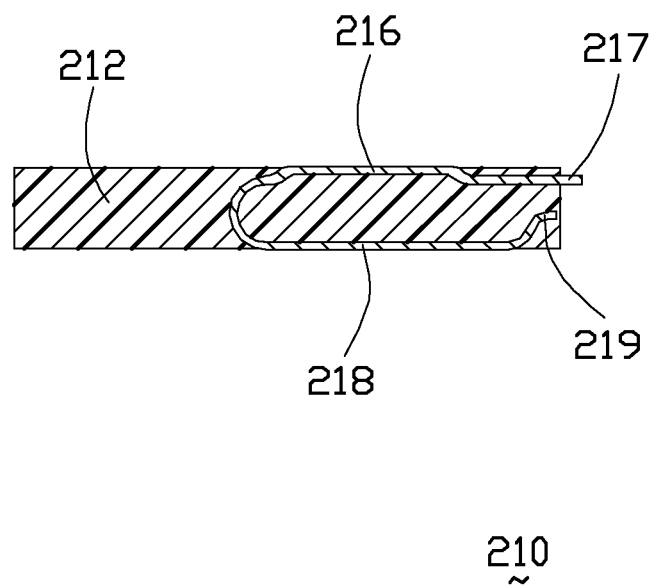
FIG. 4(A) is a cross-sectional view of the first contact module of FIG. 3(A).
Figure 4B:
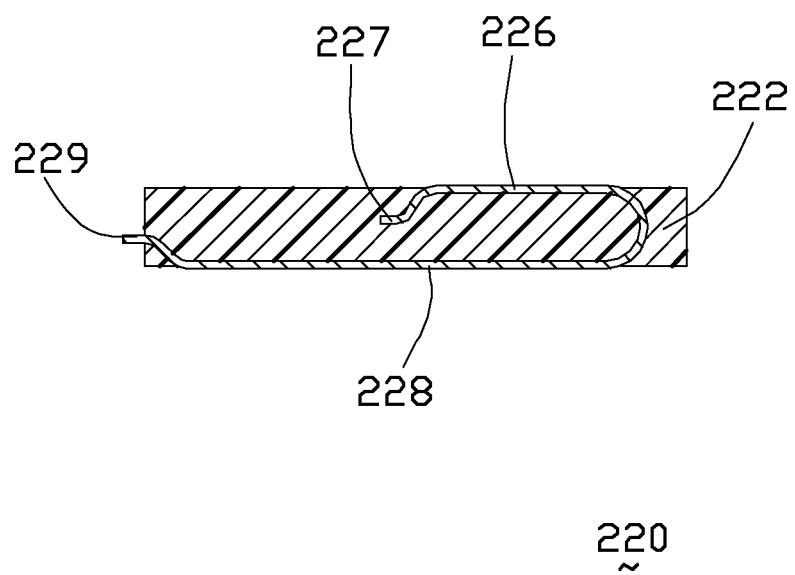
FIG. 4(B) is a cross-sectional view of the second contact module of FIG. 3(A).

Reference will now be made in detail to the preferred embodiment of the present invention. FIGS. 1(A)-4(B) shows a machine case 100 including a boat like base 202 having a first deck station 204 and a second deck station 206 respectively located at two opposite lengthwise ends of the base 202. A first contact module 210 is seated upon the first deck station 204 and a second contact module 220 is seated upon the second deck station 206.

The first contact module 210 includes a first insulator 212 retaining a plurality of first contacts 214 thereto via an insert molding process, wherein the first contact 214 is unitarily formed with a first upper contacting section 216 with a first exposed end 217 and a first lower contacting section 218 with a first embedded end 219. Similarly, the second contact 220 includes a second insulator 222 retaining a plurality of second contacts 224 thereto via another insert molding process, wherein the second contact 224 is unitarily formed with a second upper contacting section 226 with a second embedded end 227 and a second lower contacting section 228 with a second exposed end 229. In this embodiment, both the first contact 214 and the second contact 224 are made from sheet metal with bends thereof, wherein the first upper contacting section 216 is aligned with the first lower contacting section 218, and the second upper contacting section 226 is aligned with the second lower contacting section 228 in the vertical direction. Also, the first contact 214 is essentially of a folded type and the joint between the first upper contacting section 216 and the first lower contacting section 218 is embedded with the first insulator 212 in a hidden manner, the second contact 224 being as well. To retain the first contact module 210 to the first deck station 204, the first insulator 212 forms a pair of first through holes 211 and the first deck station 204 forms a pair of first posts 205 extending through the corresponding through holes 211, respectively. The first through holes 211 define different sizes, and the first posts 205 also form with different sizes corresponding to the first through holes 211 so as to prevent a mis-assembly therebetween. Similarly, the second contacts module 220 forms a pair of second through holes 221 with different sizes receiving the corresponding posts 207 with different sizes on the second deck station 206, respectively. Notably, the first insulator 212 and the second insulator 222 respectively optimally form the stepped structures (not labeled) on two opposite ends to be seated upon the corresponding shoulders (not labeled) on the corresponding first and second deck stations 204, 206. Understandably, the first exposed end 217 and the second exposed end 229 are used to originally be connected to the corresponding contact carriers 213, 223 before breaking therefrom during the insert molding process.

Figure 5A:
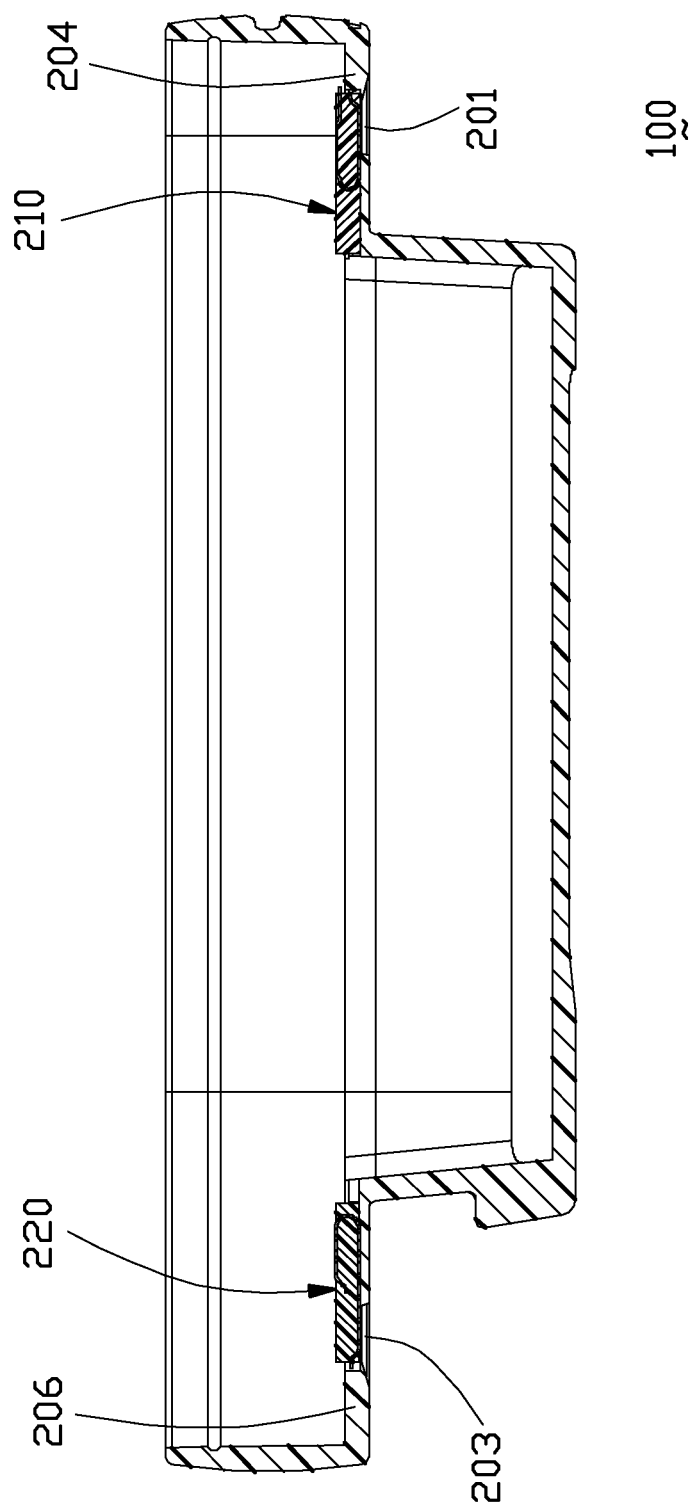
FIG. 5(A) is a cross-sectional view of the machine case of FIG. 1(A).
Figure 5B:
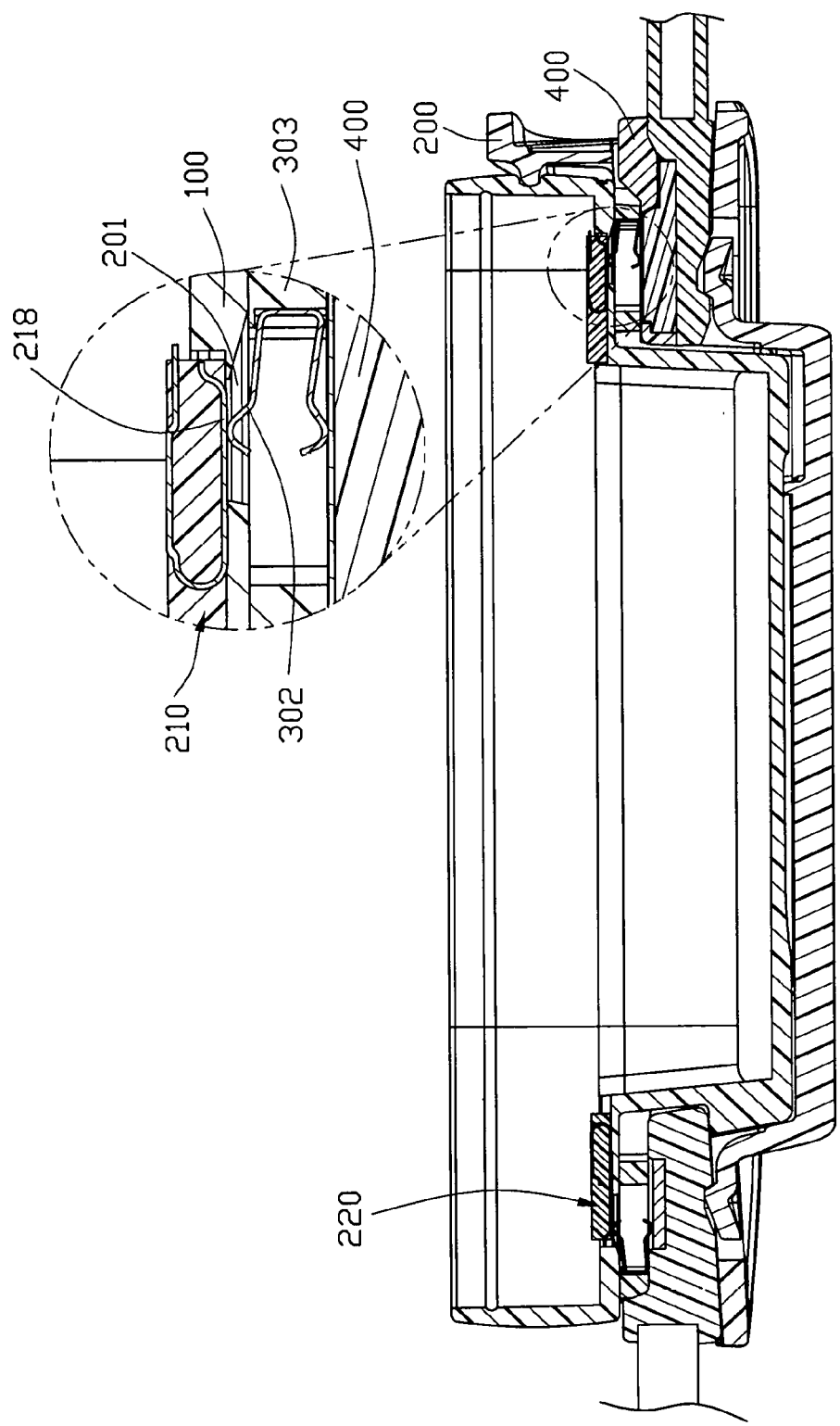
FIG. 5(B) is a cross-sectional view of the machine case of FIG. 1(A) assembled with the cradle and the associated cables disclosed in the aforementioned provisional application.
Figure 6A:
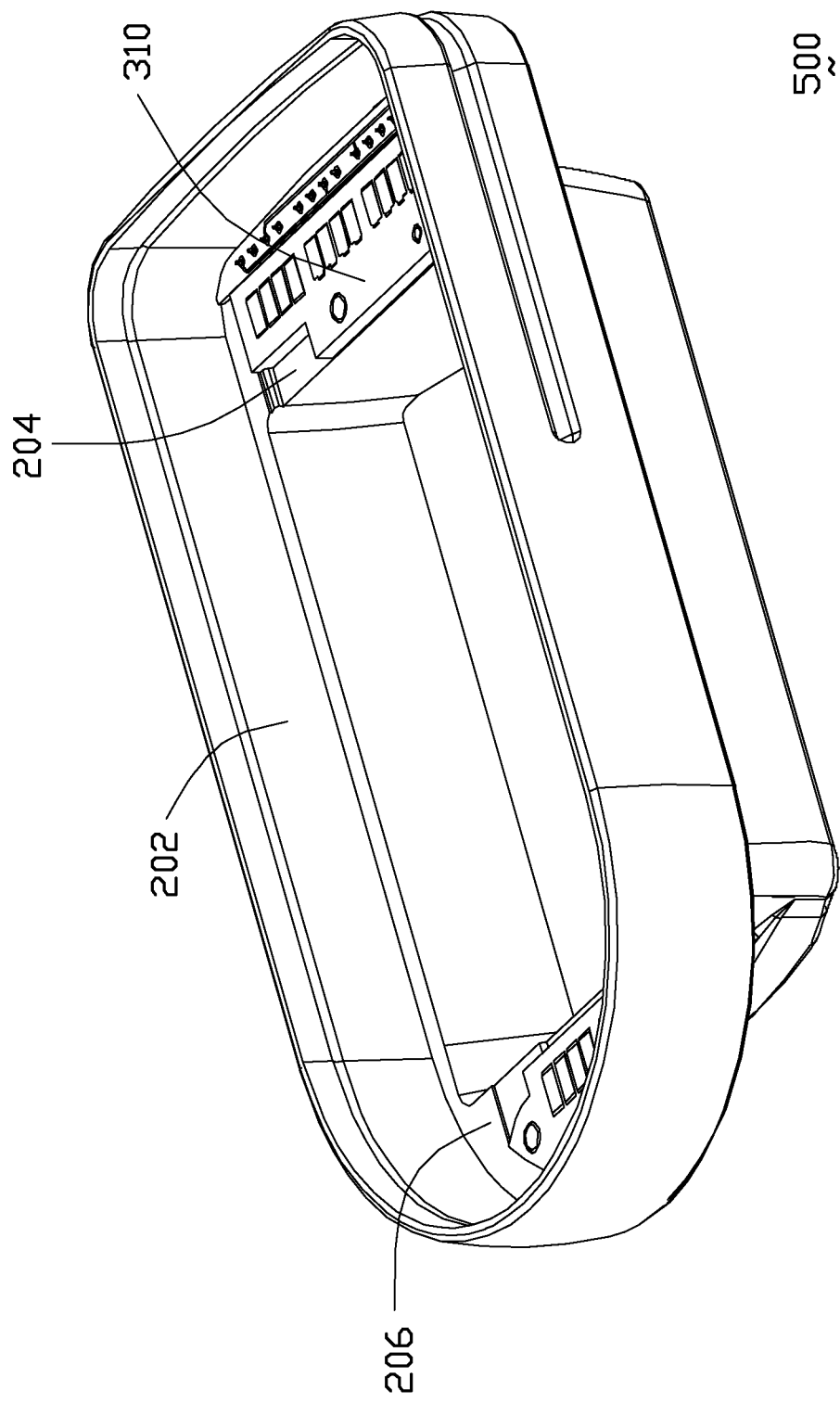
FIG. 6(A) is a downward assembled perspective view of the machine case according to a second embodiment of the invention.
Figure 6B:
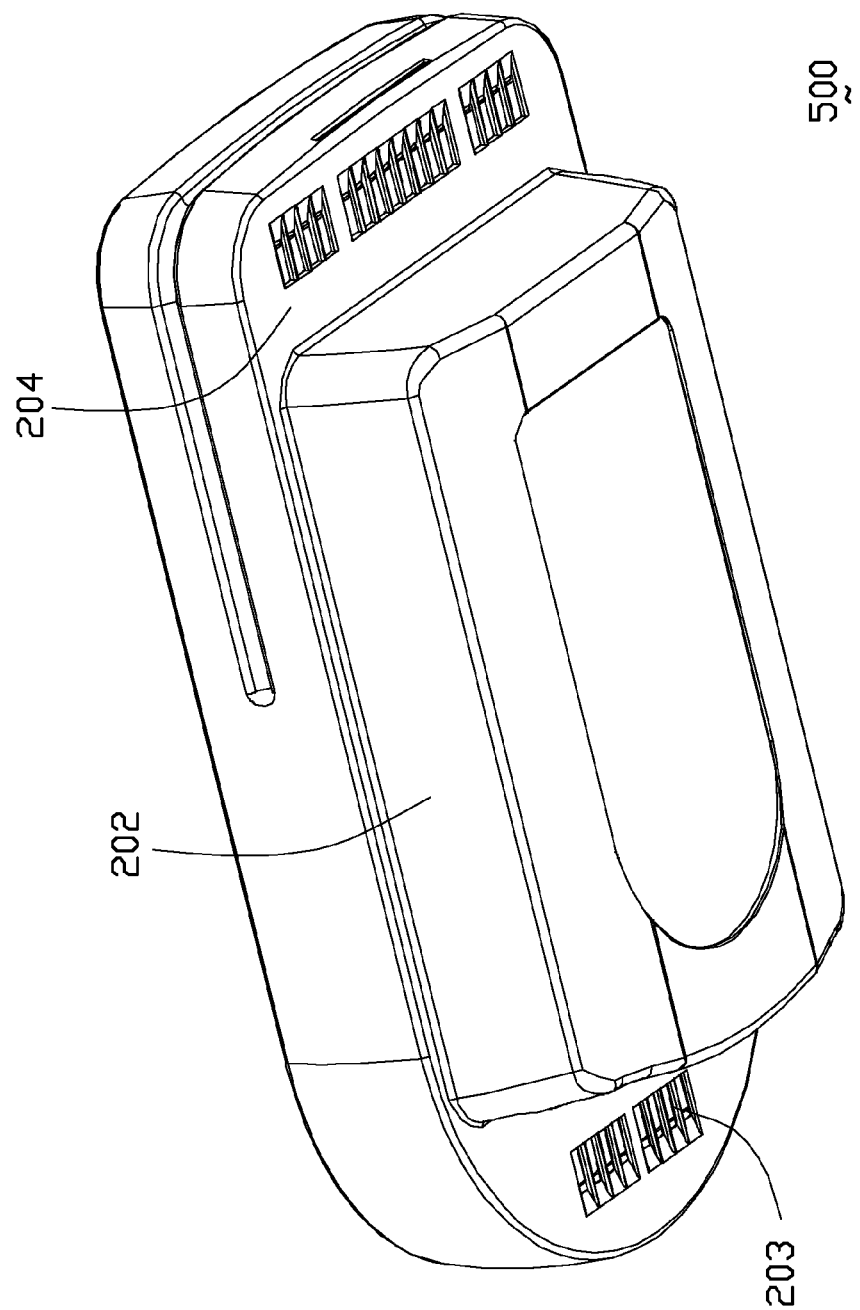
FIG. 6 (B) is an upward assembled perspective view of the machine case of FIG. 6(A).
Figure 7A:
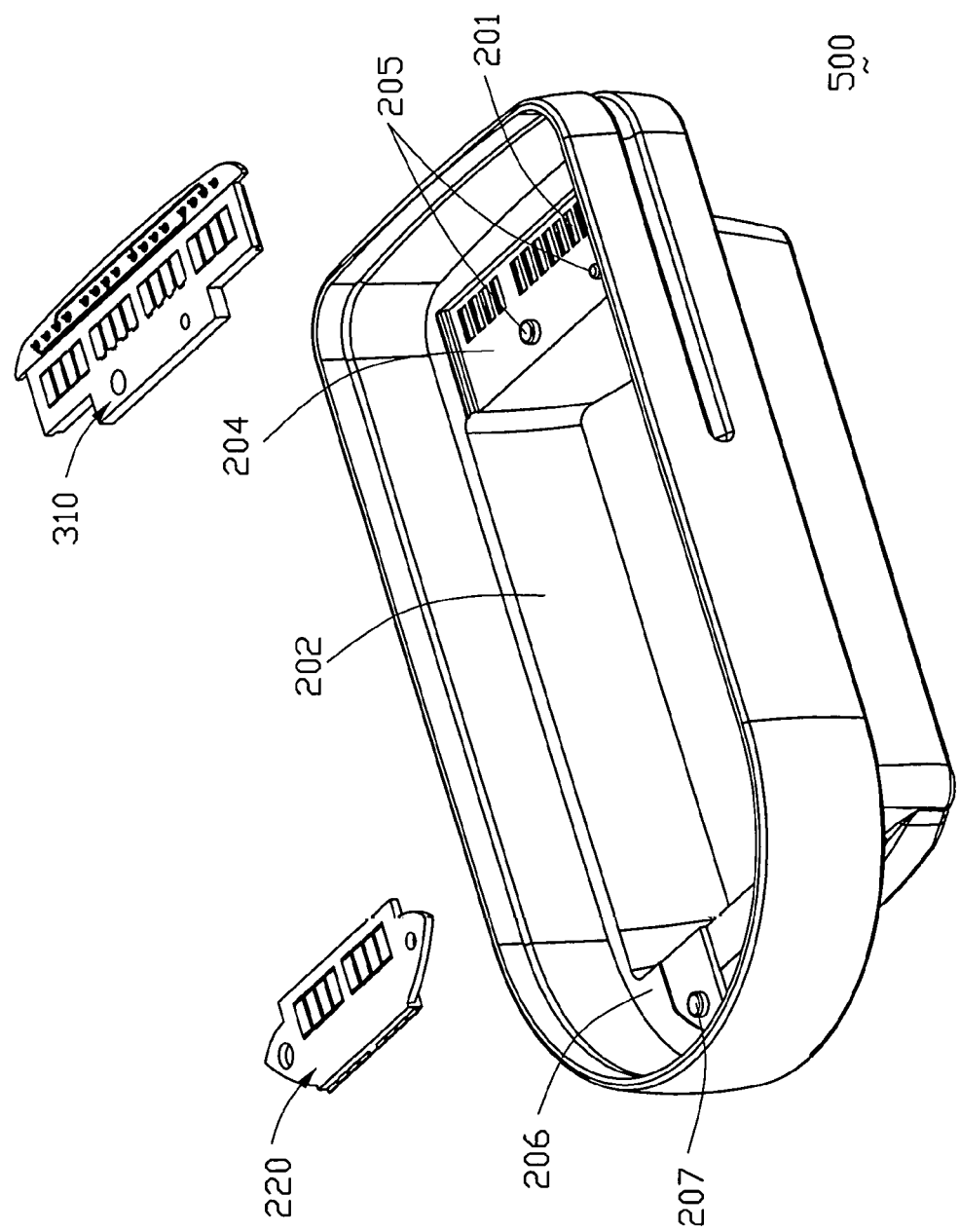
FIG. 7(A) is a downward exploded perspective view of the machine case of FIG. 6(A).
Figure 7B:
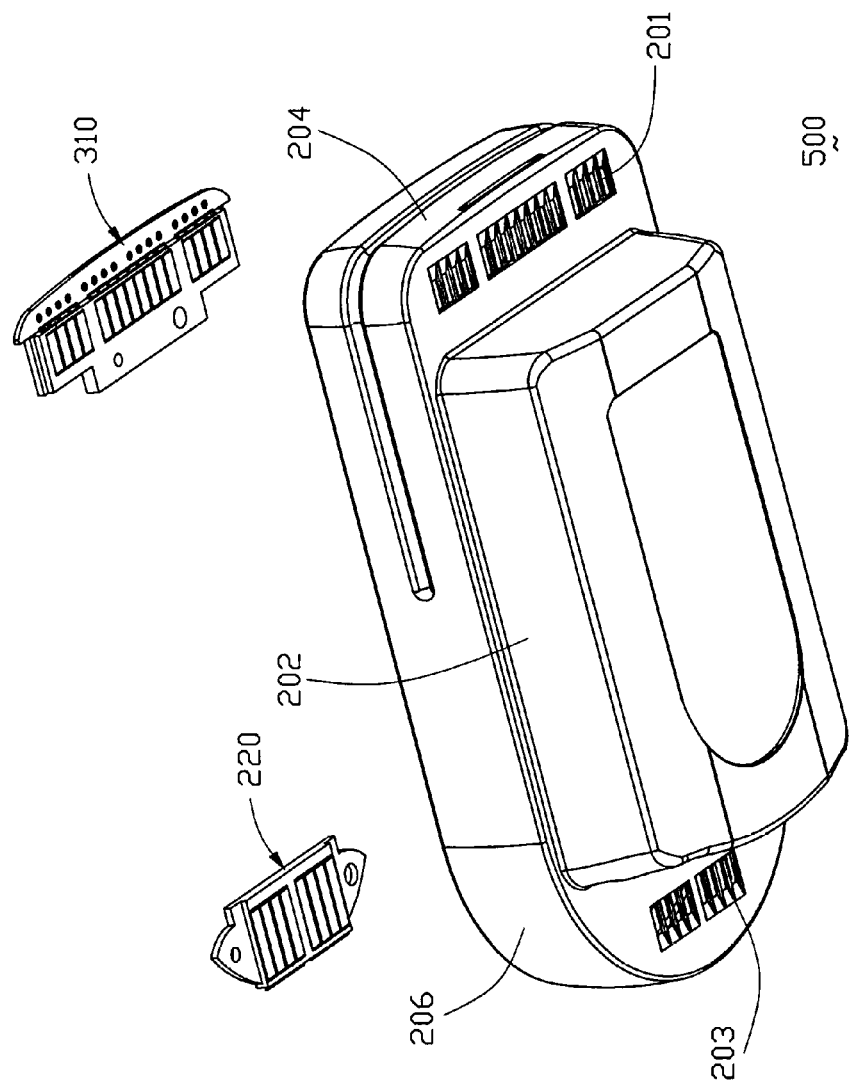
FIG. 7(B) is an upward exploded perspective view of the machine case of FIG. 7(A).
Figure 8A:
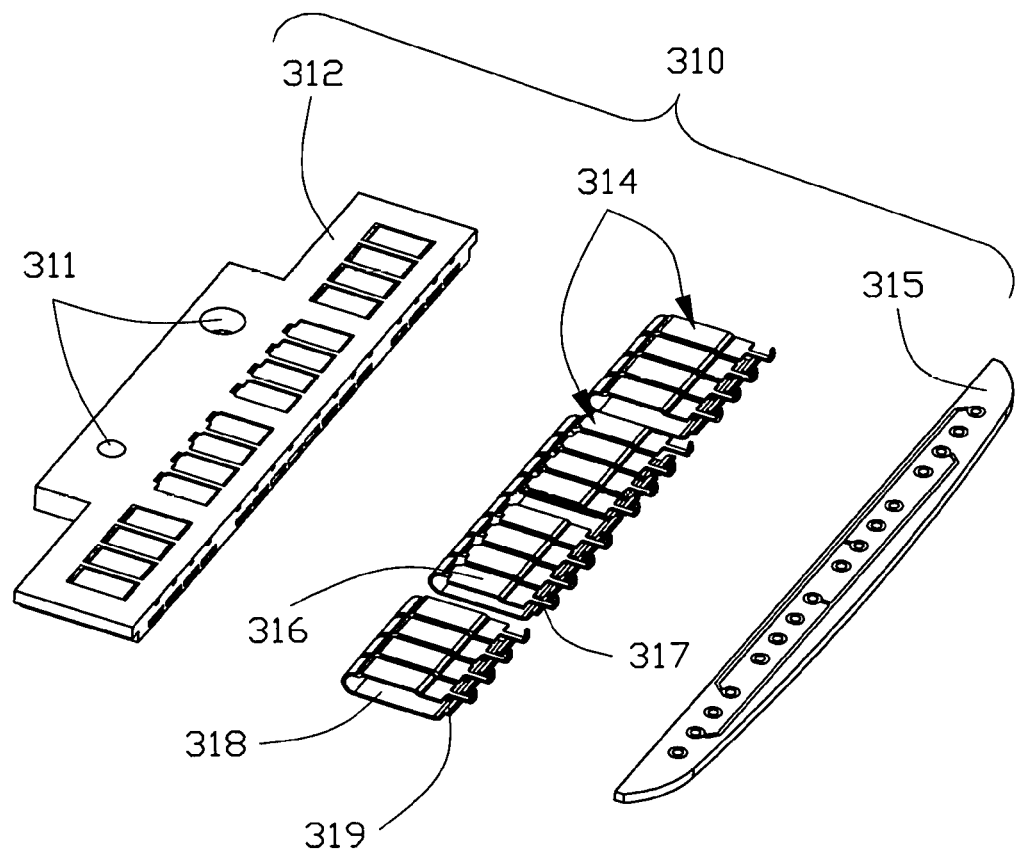
FIG. 8(A) is a downward exploded perspective view of the first contact module of the machine case of FIG. 7(A).
Figure 8B:
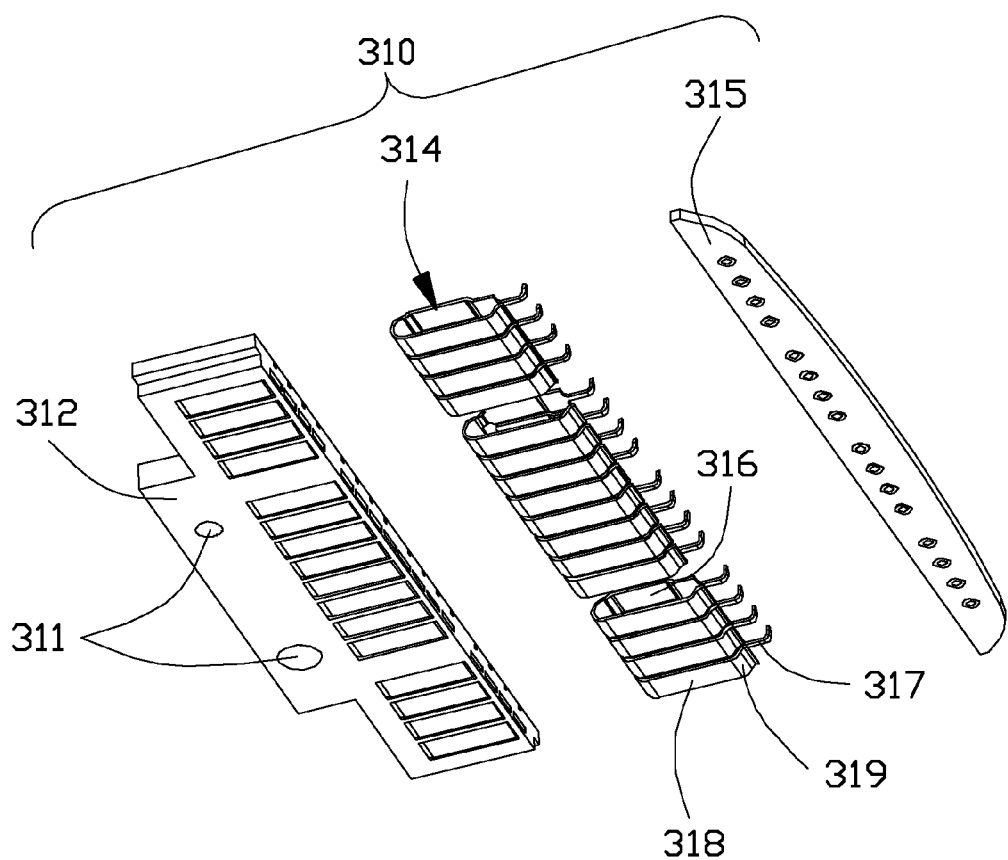
FIG. 8(B) is an upward exploded perspective view of the first contact module of FIG. 8(A).
Figure 9:
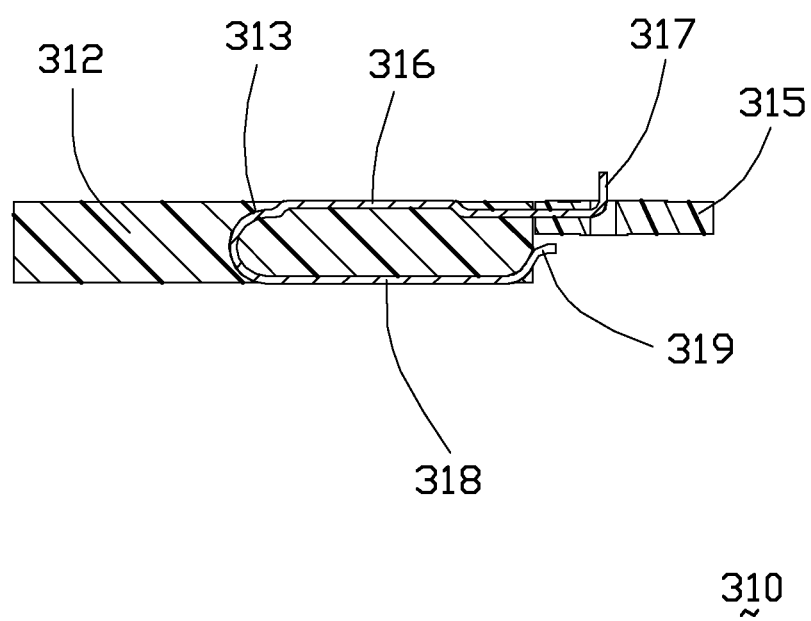
FIG. 9 is a cross-sectional view of the first contact module of FIG. 7(A).

As shown in FIGS. 5(A) and 5(B), the first deck station 204 forms a plurality of through slots 201 in alignment with the corresponding first contacts 214 in the vertical direction; similarly, the second deck station 206 forms a plurality of through slots 203 in alignment with the corresponding second contacts 224.

During using, the case 100 is positioned upon and also into a cradle 200 wherein the contact 302 of the terminal module 303 of the cradle 200 mechanically and electrically connects the first lower contacting section 218 through the corresponding through slot 201 for electrically connecting the first contact module 210 with the cable plug 400 at the first end. Similarly, the contact of another terminal module of the cradle 200 mechanically and electrically connects the second lower contacting section 228 through the corresponding through slot 203 for electrically connecting the second contact module 220 with the corresponding plug at the second end.

Figure 10:
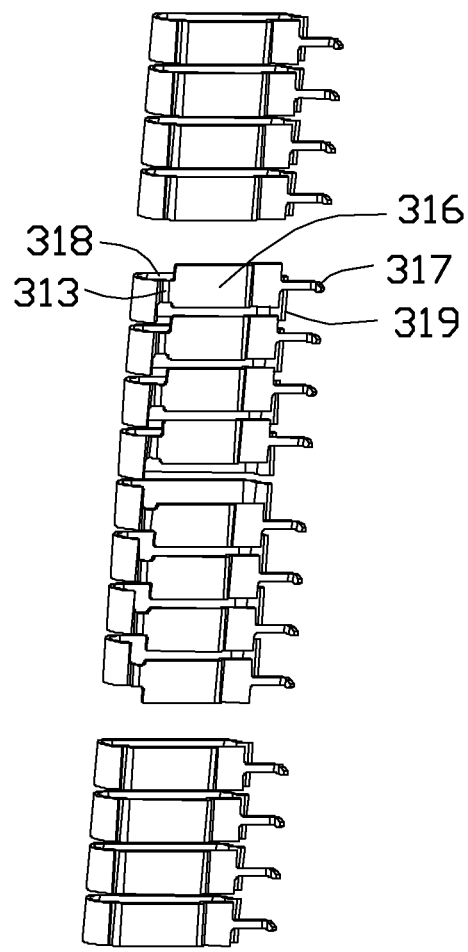
FIG. 10 is a perspective view of the first contacts to show the offset arrangement between the upper contacting section and the lower contacting section in some contacts.
Figure 10A:
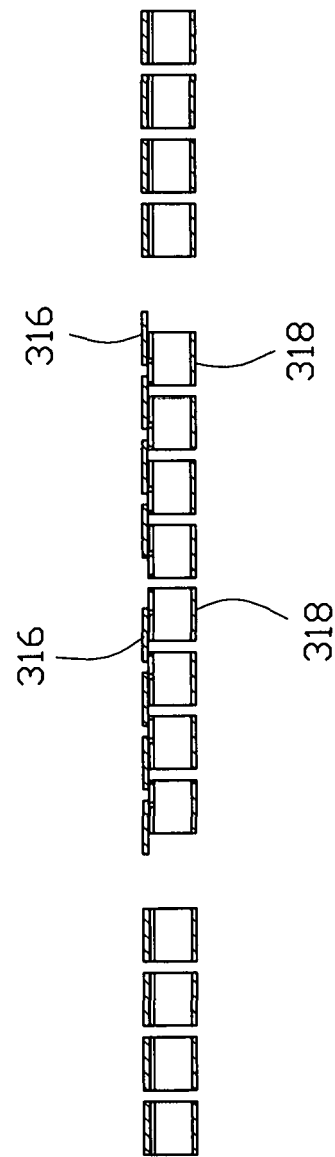
FIG. 10(A) is a cross-sectional view of the first contacts of FIG. 10.
Figure 11A:
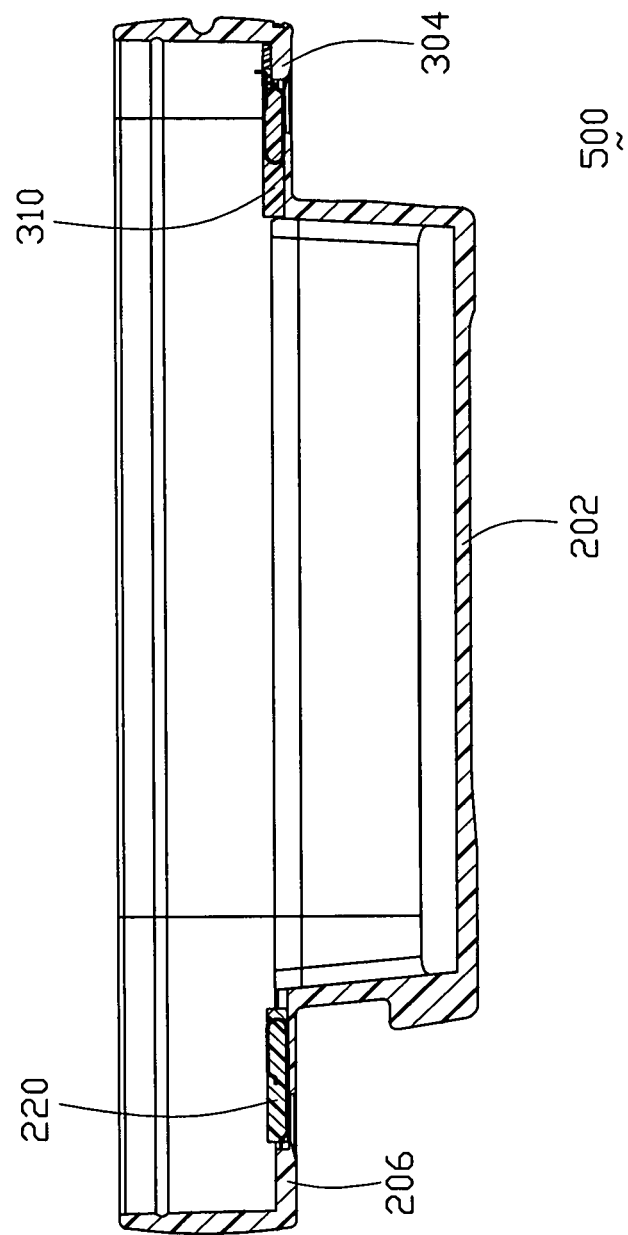
FIG. 11(A) is a cross-sectional view of the machine case of FIG. 6(A).
Figure 11B:
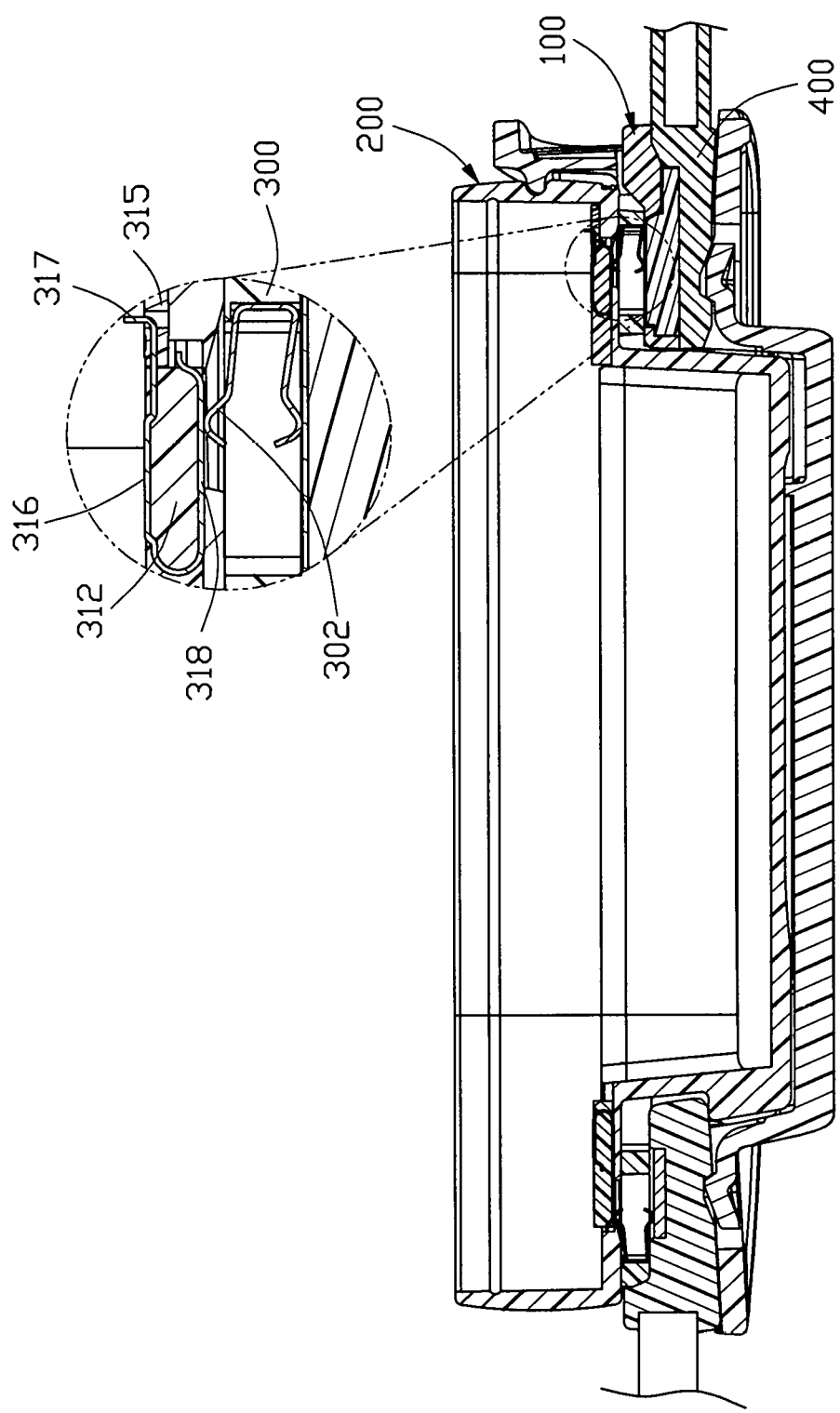
FIG. 11(B) is a cross-sectional view of the machine case of FIG. 6(A) assembled with the cradle and the associated cables disclosed in the aforementioned provisional application.
Figure 12:
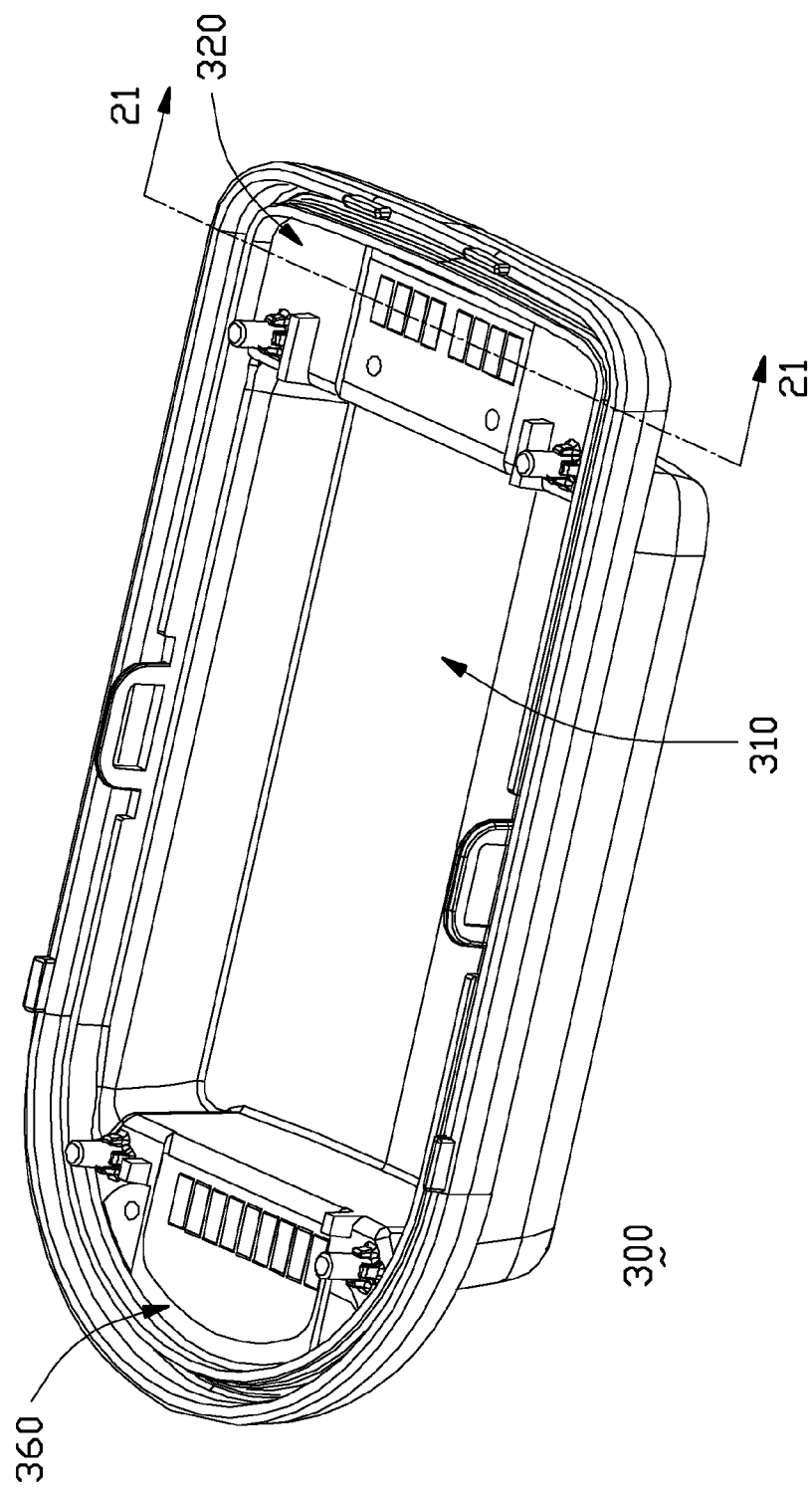
FIG. 12 is a downward perspective view of the machine case of a third embodiment of the instant invention.
Figure 13:
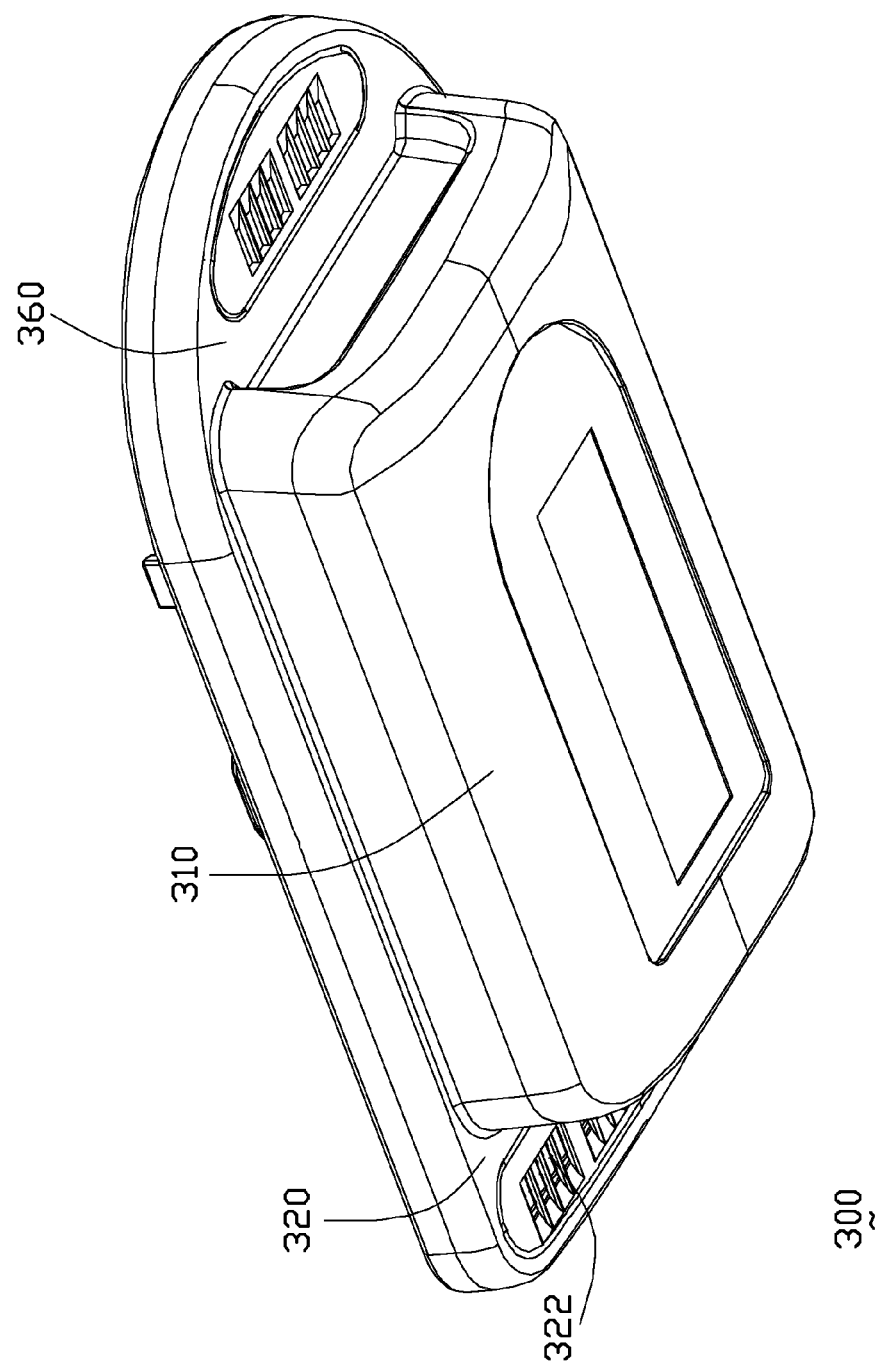
FIG. 13 is an upward perspective view of the machine case of FIG. 12.
Figure 14:
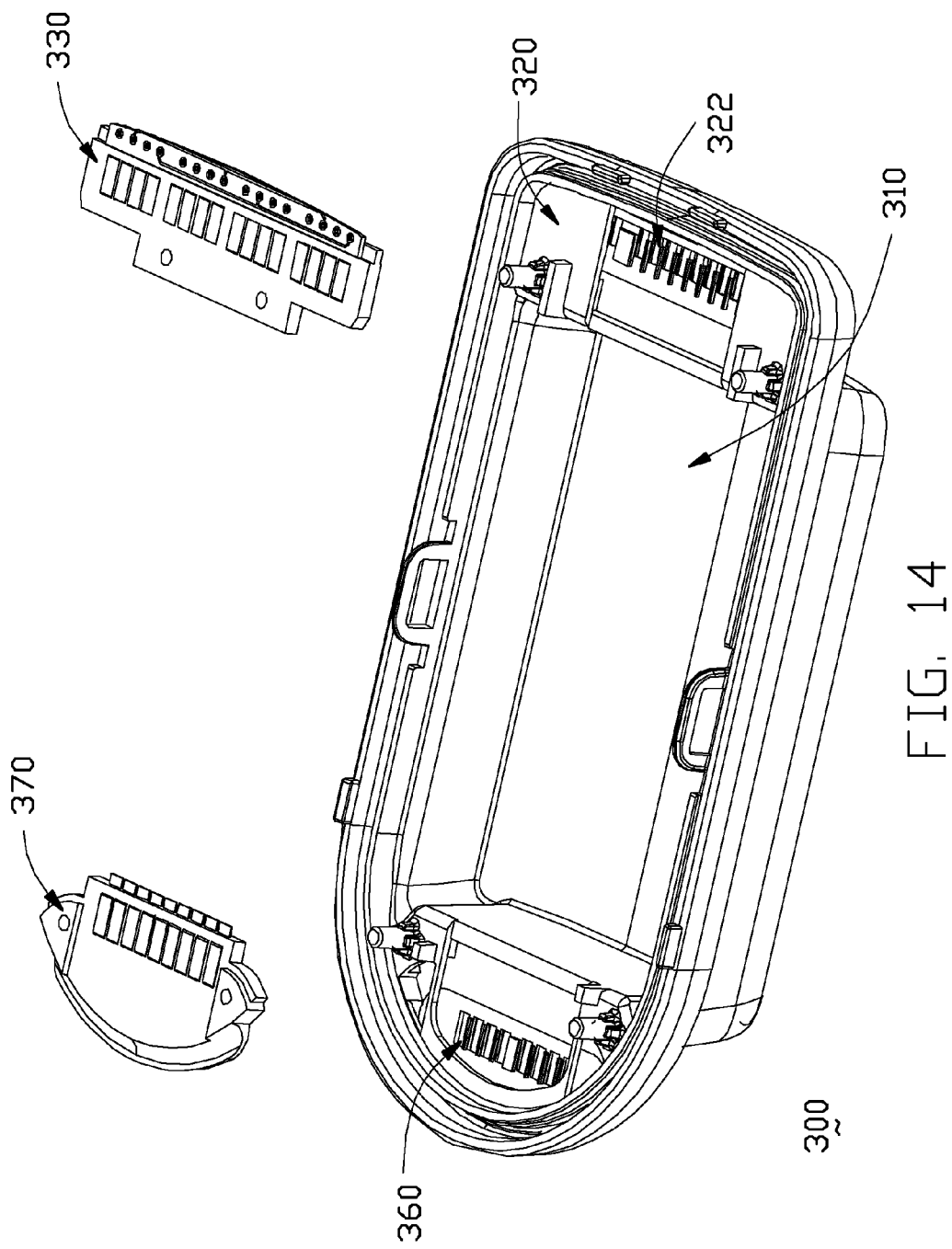
FIG. 14 is a downward exploded perspective view of the machine case of FIG. 12.
Figure 15:
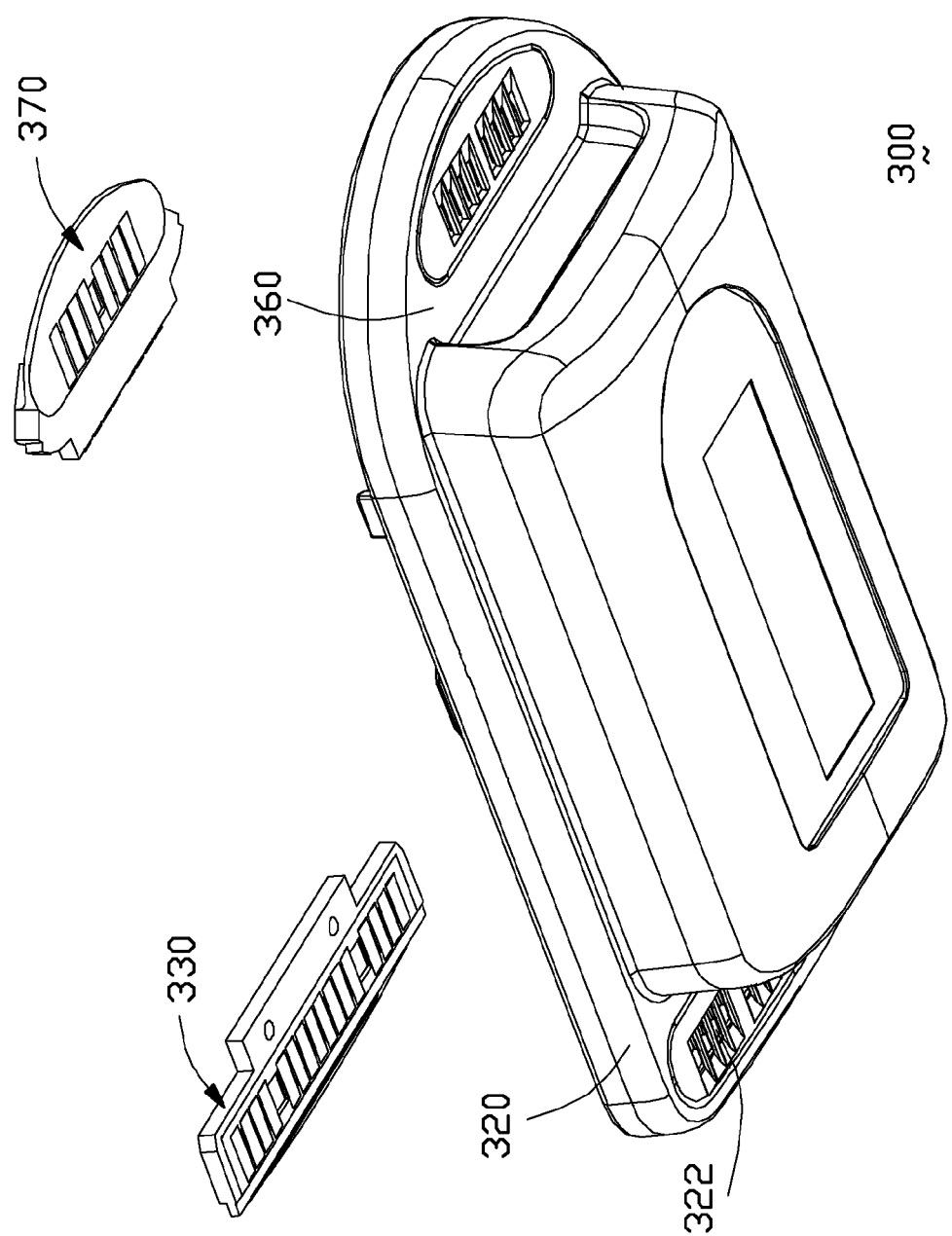
FIG. 15 is an upward exploded perspective view of the machine case of FIG. 12.
Figure 16:
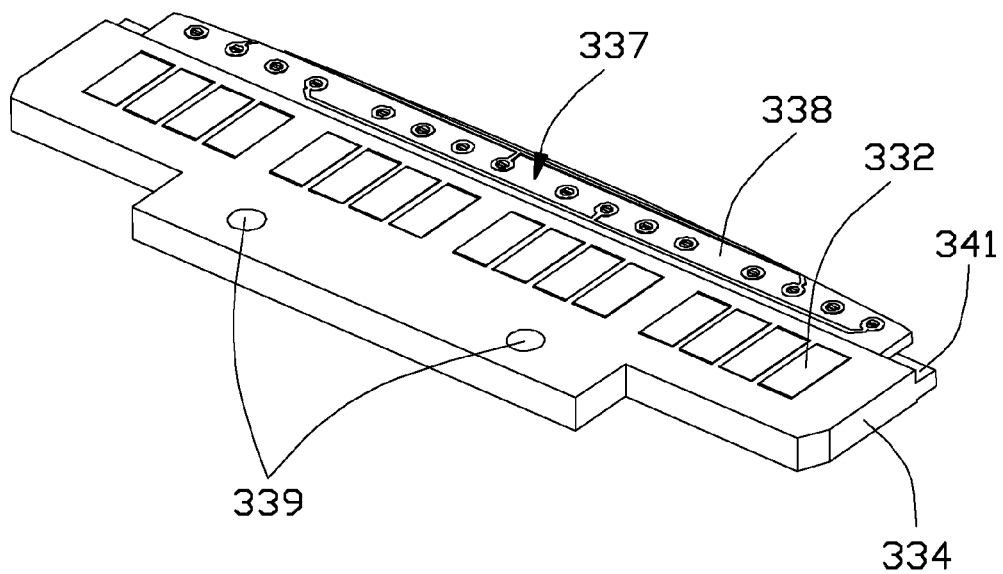
FIG. 16 is a downward perspective view of the first contact module of the machines case of FIG. 12.
Figure 17:
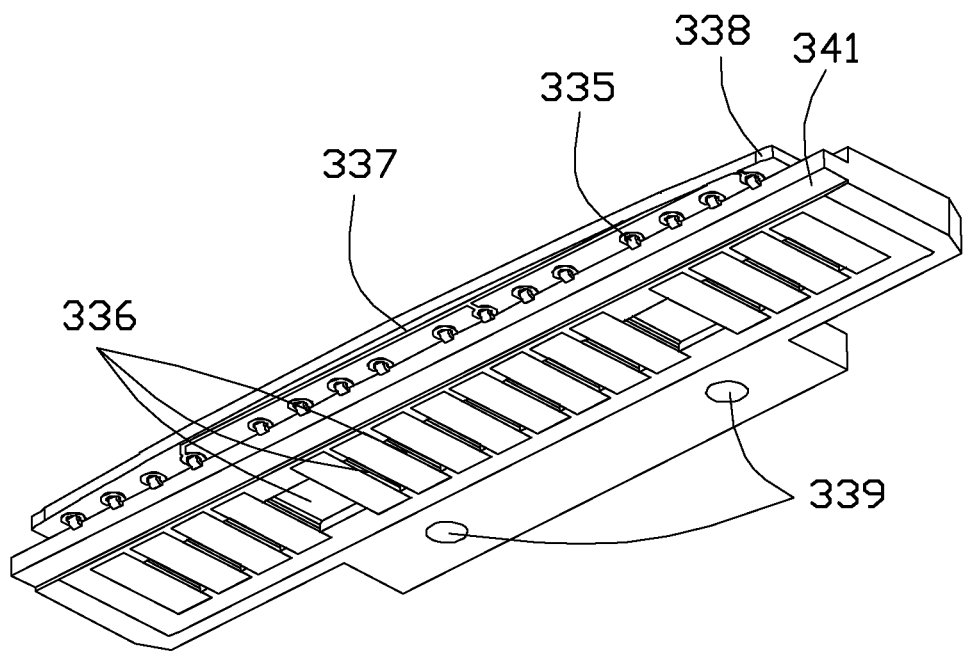
FIG. 17 is an upward perspective view of the first contact module of machine case of FIG. 12.
Figure 18:
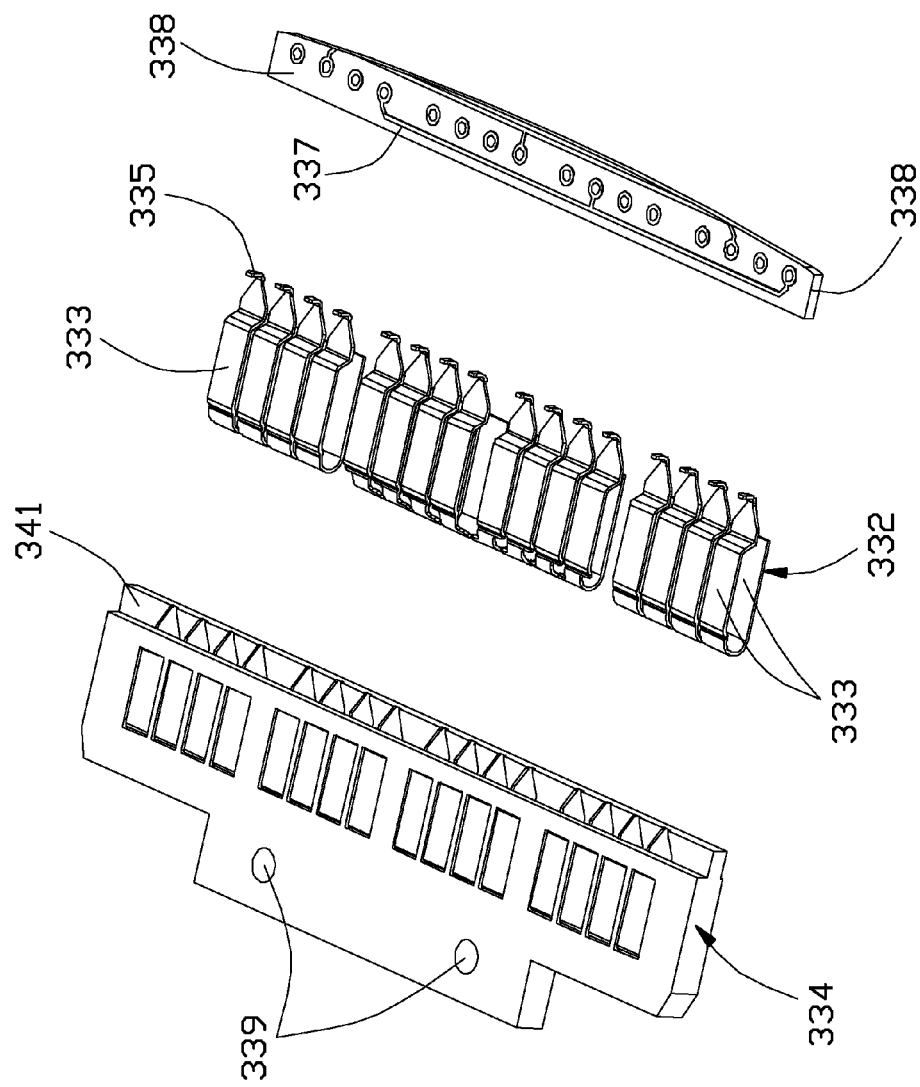
FIG. 18 is a downward exploded perspective view of the first contact module of the machine case of FIG. 12.
Figure 19:
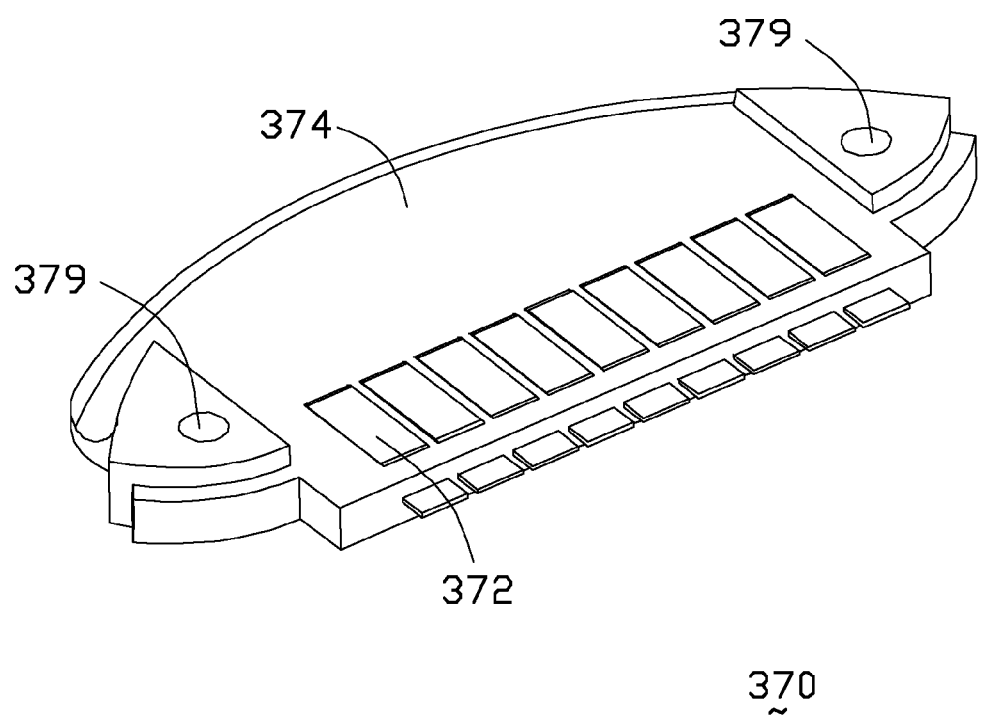
FIG. 19 is a downward perspective view of the second contact module of the machine case of FIG. 12.
Figure 20:
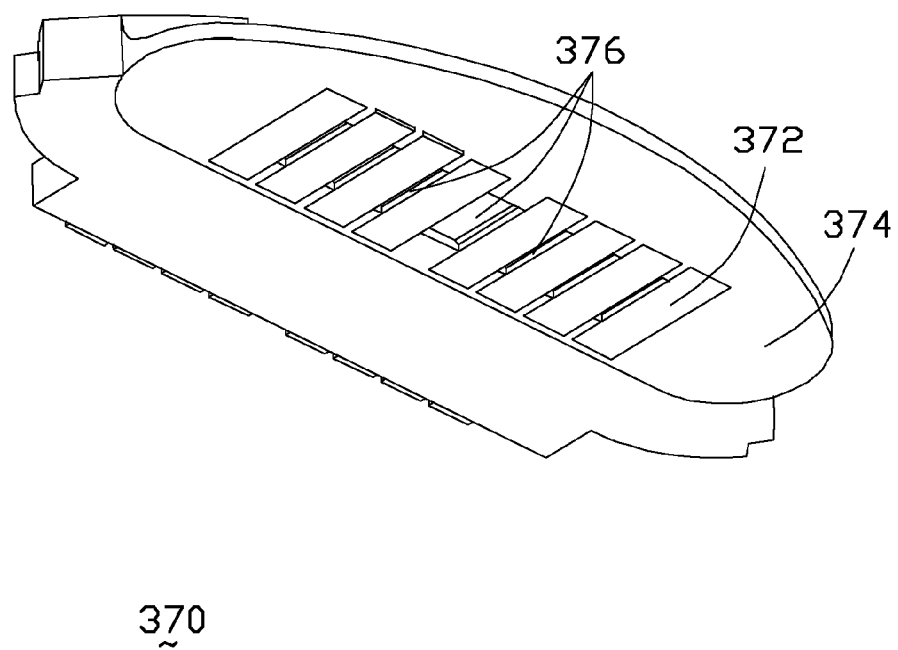
FIG. 20 is an upward perspective view of the second contact module of the machine case of FIG. 12.
Figure 21:
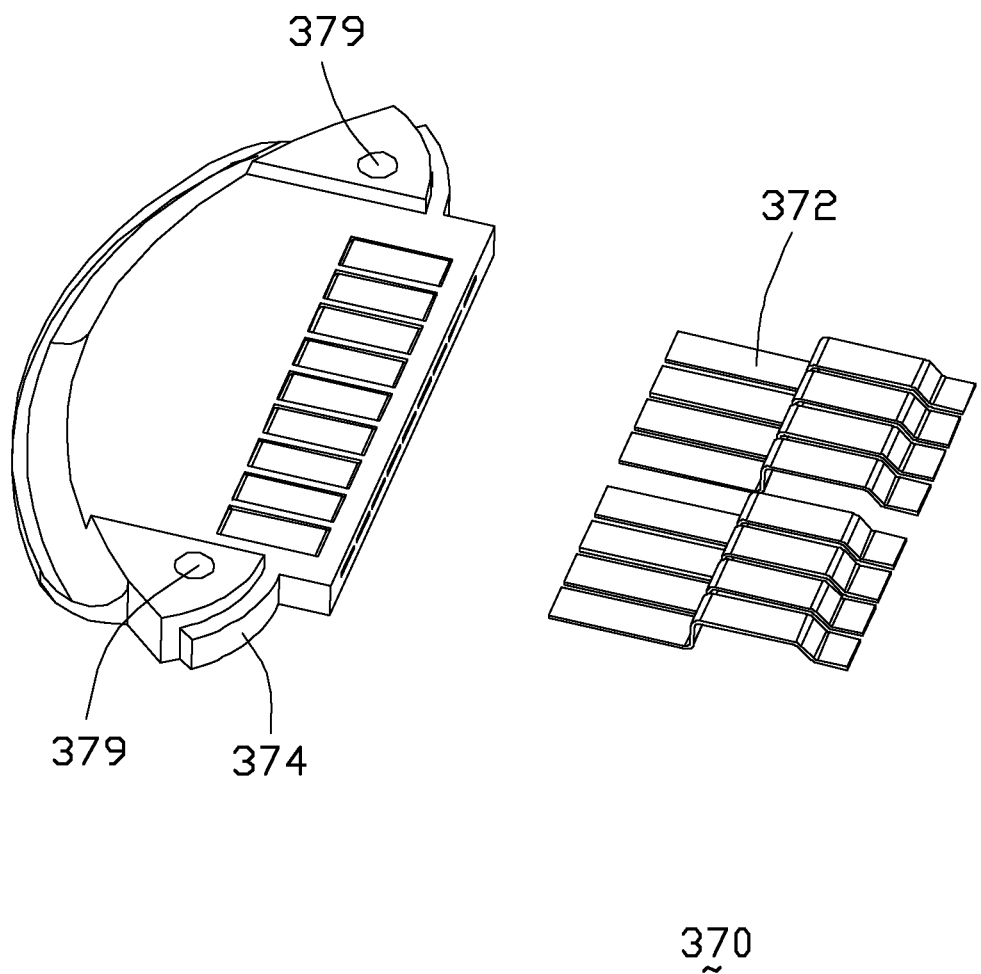
FIG. 21 is a downward perspective view of the second contact module of the machine case of FIG. 12.
Figure 22:
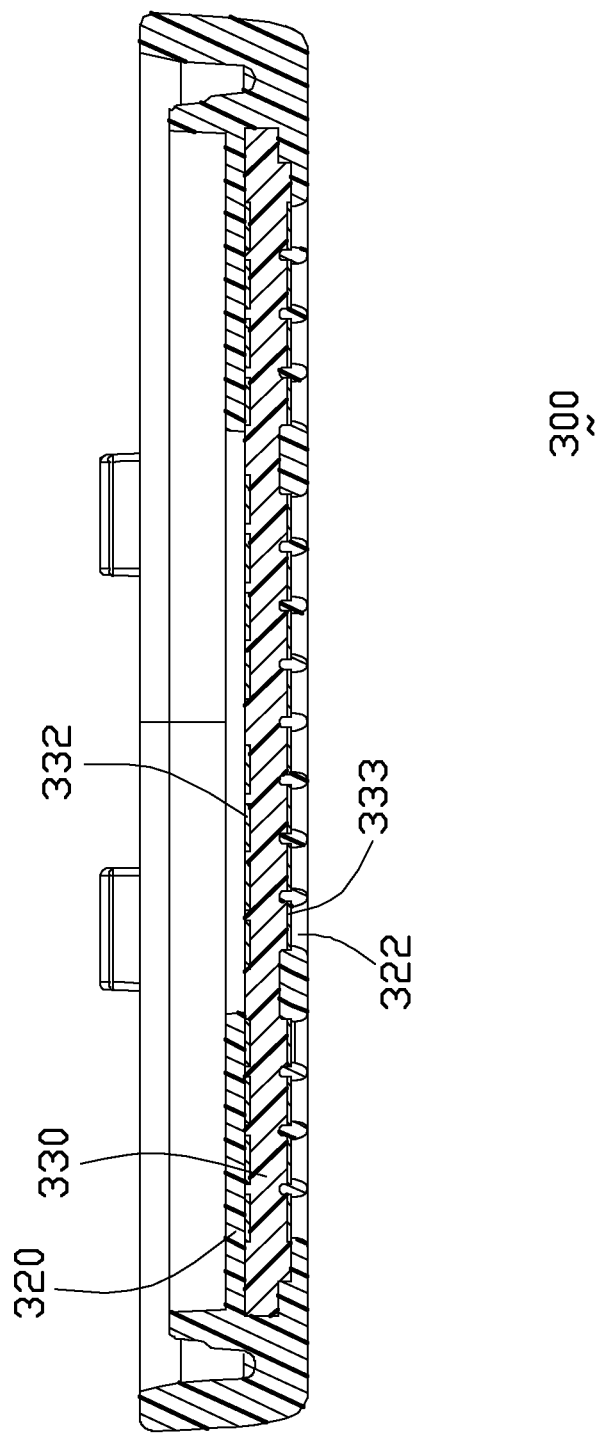
FIG. 22 is a cross-sectional view of the machine case of FIG. 12 to show the contact module is embedded within the corresponding deck station.

FIGS. 6(A)-11(B) shows a machine case 500 of a second embodiment every similar to the machine case 100 except the first contact module renumbered as 310. Therefore, the first contact module 310 will be described in detail while other parts of the machine case 500 will be omitted hereinafter. The first contact module 310 includes a first insulator 312 retaining a plurality of first contacts 314 thereto via an insert molding process, wherein the first contact 314 is unitarily formed with a first upper contacting section 316 with a first exposed end 317 and a first lower contacting section 318 with another first end 319. Different from what is disclosed in the first contact 214 of the machine case 100, the two middle sets of the first contacts 314 have oppositely offset away from each other in a symmetrical manner with regard to a centerline therebetween, wherein in each first contact the first upper contacting section 316 and the first lower contacting section 318 are only partially aligned with each other in the vertical direction and being offset from each other in the transverse direction. Notably, to ease manufacturing, a bight 313 as shown in FIG. 10, linked between the first upper contacting section 316 and the first lower contacting section 318 has a portion narrower than the first upper contacting section 316 and the first lower contacting section 318. Further, the first contact module 310 further includes a printed circuit board 315, with traces for shorting/connecting some selected first contacts 314 together, on which the first exposed ends 317 of the first upper contacting sections 216 are mounted.

Referring to FIGS. 12-21, a machine case 300 of a third embodiment similar to the machine case 100 except the first contact module 330 and the second contact module 370. The first contact module 330 is insert-molded within the first deck station 320, and the second contact module 370 is insert-molded within the second deck station 360. Compared with the embodiments disclosed in the machine case 100, the feature of this embodiment is to have the corresponding contact modules embedded within the corresponding deck stations via the molding process forming the main portion and the deck stations, rather than mounting thereon after the deck stations have been formed by the corresponding molding process. Therefore, this embodiment uses the method of the so-called two shots or two insert-moldings to have the contact module of the first insert-molding reliably retained within the corresponding deck stations via the second insert-molding, compared with the embodiments disclosed in the machine case 100 using one insert molding to form the contact module which is retained upon the corresponding deck station which has been formed via an injection molding.

Similar to the embodiments disclosed in the machine case 100, the first contact module 330 includes a plurality of first contacts 332 embedded within the corresponding first insulator 334 via an insert molding process. Anyhow, different from the embodiments in the machine case 100, in the bottom surface of the insulator 334 the partitions or recesses 336 between every adjacent two first contacts 332 are emptied for allowing the core-pins of the mold to occupy during the first insert-molding process for assuring true positions of the corresponding contacts with regard to the first insulator 334. Notably, such recesses 336 are filled with the material of the deck station 320 via the second insert-molding process during forming the main portion 310 and the first deck station 320 and the second deck station 360. Understandably, in this embodiment the recesses 336 are shorter than the contacting regions 333 of the neighboring first contacts 332 in the longitudinal direction, anyhow, alternately are longer, if necessary. Also, the recesses 336 may be applied to the upper surface of the first insulator 334, if necessary.

Similar to the embodiments disclosed in the machine case 500, a transitional printed circuit board 338 is positioned upon the first insulator 334 and mechanically and electrically connected to tails 335 of the corresponding contacts 332 to selectively short some of them via corresponding traces 337. The transitional printed circuit board 338 is further secured by the first deck station 320 after the second insert molding process. A flange structure 341 is formed on the first insulator 334 to support the transitional printed circuit board 338. A pair of alignment holes 339 with same sizes are formed in the first insulator 334 for holding the first contact module 330 in position during the second insert-molding process in which the first deck station 320 is formed with the first contact module 330 embedded therein. Notably, two lateral regions of the upper surface of the first contact module 330 including the contacting regions 333 of the corresponding first contacts 332, are covered by the material of the first deck station 320 in the vertical direction. Anyhow, the contacting regions 333 of the first contacts 332 on the bottom surface of the first insulator 334 are still downwardly exposed to an exterior through the corresponding openings 322. Similar to what is disclosed in the embodiments of the provisional applications, in the first contact module 330, the contacting regions 333 of the eight first contacts 332 in a center region on the upper surface are divided into two groups to be essentially offset away from each other while those on the bottom surface are still located in the original positions. Therefore, for each of those eight first contacts, the contacting region 333 on the upper surface and that on the bottom surface are not aligned with each other in the vertical direction but in an offset manner. Understandably, because these two groups are symmetrical with each other, only one stamping mold is required for manufacturing.

Similarly, the second contact module 370 includes a plurality of second contacts 372 embedded within the second insulator 374. The second insulator 374 forms a plurality of recesses 376 formed between the neighboring contacts 372 for positioning of the core-pins of the mold during the first insert-molding and successively filled with the material of the second deck station 360 during successively insert-molding the second contact module 370 with the second deck station 360. A pair of alignment holes 379 are formed within the second insulator 374 for holding the second contact module 370 in position during the second insert-molding in which the second deck station 360 is formed with the second contact module 370 embedded therein.

It should be noted that even though in the embodiment the machine case and the cradle are involved and disclosed, the instant invention is essentially and primarily related to the contact module and the connection parts only, so other portions may be others' invention. For example, the contacts can be stamped from Stainless Steel or Phos. Bronze and/or be plated with such coatings as Titanium Nitride or Rhodium to reduce corrosion when being used in harsh conditions. It should be noted that the invention is essentially related to the contact module only and other portions of the machine case and the cradle may be others' invention.

What is claimed is:
1. An electrical connector for use within a machine case comprising:
   an insulator defining opposite top and bottom surfaces thereon in a vertical direction;
   a plurality of contacts retained to the insulator via an insert molding process and arranged along a transverse direction perpendicular to said vertical direction, each of said contacts stamped and bent from sheet metal and unitarily formed with an upper contacting section exposed upon the top surface, and a lower contacting sections exposed upon the bottom surface, each of said upper contacting section and said lower contacting section extending along a longitudinal direction perpendicular to both said vertical direction and said transverse direction; wherein
   each of the upper contacting section and the lower contacting section is planar and stationary; wherein one of said upper contacting section and said lower contacting section defines an outer end exposed to an exterior for originally linking to a contact carrier; wherein said some of the contacts are divided into at least two opposite groups, and the upper contacting sections in one group are offset away from those in the other group in said transverse direction in a symmetrical manner with regard to a centerline between said two groups.

2. The electrical connector as claimed in claim 1, wherein said lower contacting section is longer than the upper contacting section in the longitudinal direction.

3. The electrical connector as claimed in claim 1, wherein each contact of said two groups is of a folded type with a joint linking the upper contacting section and the lower contacting section, and said joint is embedded with the insulator and hidden from the exterior and narrower than either the upper contacting section and the lower contacting section in the transverse direction.

4. The electrical connector as claimed in claim 1, wherein said outer ends extend from the respective upper contacting sections and are commonly connected to a printed circuit board with traces connecting/shorting the outer ends of the upper contacting sections of the selected contacts.

5. The electrical connector as claimed in claim 4, wherein the insulator has a flange structure extending therefrom with the printed circuit board supported on an upper surface thereof, said outer ends are positioned on said upper surface of the flange structure.

6. The electrical connector as claimed in claim 1, wherein the insulator defines a plurality of recesses formed on at least one of the top and bottom surfaces and located between the neighboring contacts.

7. A machine case comprising:
a base having a first deck station and a second deck station respectively located at two opposite ends of the base in a longitudinal direction;
a first contact module seated upon the first deck station and comprising a first insulator defining opposite first top and bottom surfaces thereon in a vertical direction, and a plurality of first contacts retained to the first insulator via a first insert molding process and arranged along a transverse direction perpendicular to said vertical direction and longitudinal direction; each of said first contacts defining a first upper contacting section exposed upon the first top surface, and a first lower contacting section exposed upon the first bottom surface, each of said first upper contacting sections extending in a length along the longitudinal direction shorter than that of said lower contacting sections;
a second contact module seated upon the second deck station and comprising a second insulator defining opposite second top and bottom surfaces thereon in said vertical direction, and a plurality of second contacts retained to the second insulator via the first insert molding process and arranged along the transverse direction; each of said second contacts defining a second upper contacting section exposed upon the second top surface, and a second lower contacting section exposed upon the second bottom surface, each of said second upper contacting sections extending in a length along the longitudinal direction shorter than that of said second lower contacting sections.

8. The machine case as claimed in claim 7, wherein the first and second contact modules are embedded into the first and second deck stations respectively via a second insert molding process.

9. The machine case as claimed in claim 8, wherein the first contacts are divided into two outer groups for originally linking to one contact carrier, and two inner groups arranged between the two outer groups for originally linking to another contact carrier; the first upper contacting sections in one inner group are offset away from those in the other inner group in said transverse direction in a symmetrical manner with regard to a centerline between said two inner groups.

10. The machine case as claimed in claim 9, wherein each of said first contacts is of a folded type with a joint linking the first upper contacting section and the first lower contacting section and hidden within the insulator, said joint of each first contact in the two inner groups is narrower than either the first upper contacting section or the first lower contacting section in the transverse direction.

11. The machine case as claimed in claim 9, wherein the first upper contacting sections of the two outer groups are covered by material of the first deck station while the first upper contacting sections of the two inner groups and all of the first lower contacting sections are exposed to exterior.

12. The machine case as claimed in claim 8, wherein each of the first and second insulators defines a plurality of recesses on the respective first and second bottom surfaces and located between every adjacent two first and second contacts respectively, and the recesses are filled with the material of the first and second deck stations in the second inert molding process.

13. A machine case comprising:
a base having at least one deck station at one end along a longitudinal direction;
a contact module seated upon the deck station and comprising an insulator defining opposite top and bottom surfaces thereon in a vertical direction perpendicular to said longitudinal direction, a plurality of contacts embedded within the insulator via an insert molding process and arranged with one another along a transverse direction perpendicular to both said longitudinal direction and said vertical direction, each of said contacts having an upper contacting section exposed upon the top surface, and a lower contacting section exposed upon the bottom surface; and
a transitional printed circuit board intimated position upon the insulator; wherein
some contacts having corresponding tail sections linked to the transitional printed circuit board and shorted together.

14. The machine case as claimed in claim 13, wherein the transitional printed circuit board is located along an elongated edge of the insulator extending in the transverse direction.

15. The machine case as claimed in claim 14, wherein said transitional printed circuit board is located on an outer side of the insulator in said longitudinal direction.

16. The machine case as claimed in claim 13, wherein the deck station forms a plurality of through holes extending in the vertical direction to expose the corresponding lower contacting sections, respectively.

17. The machine case as claimed in claim 13, wherein the tail sections of said contacts extend in the vertical direction through corresponding through holes in the transitional printed circuit board.

18. The machine case as claimed in claim 13, wherein the deck station forms a large post and a small post, and the transitional printed circuit board forms a large hole and a small hole respectively receiving said large post and said small post.

19. The machine case as claimed in claim 13, wherein in each contact, the upper contacting section and the lower contacting section are not only different from each other in length along the longitudinal direction but also offset from each other in the transverse direction.

* * * * *